US011319378B2

(12) United States Patent
Liu et al.

(10) Patent No.: US 11,319,378 B2
(45) Date of Patent: May 3, 2022

(54) ANTI-PD-1/ANTI-HER2 NATURAL ANTIBODY STRUCTURAL HETERODIMERIC BISPECIFIC ANTIBODY AND METHOD OF PREPARING THE SAME

(71) Applicant: BEIJING HANMI PHARMACEUTICAL CO., LTD., Beijing (CN)

(72) Inventors: Jiawang Liu, Beijing (CN); Nanmeng Song, Beijing (CN); Yaping Yang, Beijing (CN); Maengsup Kim, Beijing (CN)

(73) Assignee: BEIJING HANMI PHARMACEUTICAL CO., LTD., Beijing (CN)

( * ) Notice: Subject to any disclaimer, the term of this patent is extended or adjusted under 35 U.S.C. 154(b) by 241 days.

(21) Appl. No.: 16/461,646

(22) PCT Filed: Nov. 16, 2017

(86) PCT No.: PCT/CN2017/111310
§ 371 (c)(1),
(2) Date: May 16, 2019

(87) PCT Pub. No.: WO2018/090950
PCT Pub. Date: May 24, 2018

(65) Prior Publication Data
US 2019/0367633 A1 Dec. 5, 2019

(30) Foreign Application Priority Data
Nov. 18, 2016 (CN) .......................... 201611016435.0

(51) Int. Cl.
C07K 16/00 (2006.01)
C07K 16/30 (2006.01)
C07K 16/32 (2006.01)
C07K 16/46 (2006.01)

(52) U.S. Cl.
CPC .............. C07K 16/30 (2013.01); C07K 16/32 (2013.01); C07K 16/46 (2013.01); C07K 2317/31 (2013.01); C07K 2317/52 (2013.01); C07K 2317/55 (2013.01); C07K 2317/622 (2013.01); C07K 2317/76 (2013.01)

(58) Field of Classification Search
CPC ........ C07K 16/30; C07K 16/32; C07K 16/46; C07K 2317/31; C07K 2317/52; C07K 2317/55; C07K 2317/622; C07K 2317/76; C07K 2317/524; C07K 2317/526; C07K 16/28; A61P 35/00
See application file for complete search history.

(56) References Cited

U.S. PATENT DOCUMENTS

| | | | |
|---|---|---|---|
| 5,173,168 A | 12/1992 | van Haastrecht et al. | |
| 5,731,168 A | 3/1998 | Carter et al. | |
| 5,869,046 A * | 2/1999 | Presta ................... | C07K 16/00 424/133.1 |
| 8,354,509 B2 | 1/2013 | Carven et al. | |
| 9,562,109 B2 | 2/2017 | Von Kreudenstein et al. | |
| 9,574,010 B2 | 2/2017 | Spreter Von Kreudenstein et al. | |
| 9,732,155 B2 | 8/2017 | Spreter Von Kreudenstein et al. | |
| 9,758,805 B2 | 9/2017 | De Kruif et al. | |
| 9,914,785 B2 | 3/2018 | Corper et al. | |
| 9,988,460 B2 | 6/2018 | Spreter Von Kreudenstein et al. | |
| 10,344,050 B2 | 7/2019 | Gramer et al. | |
| 2006/0074225 A1 | 4/2006 | Chamberlain et al. | |
| 2006/0280747 A1 | 12/2006 | Fuh et al. | |
| 2013/0195849 A1 | 8/2013 | Spreter Von Kreudenstein et al. | |
| 2013/0336981 A1 | 12/2013 | De Kruif et al. | |
| 2015/0203579 A1 | 7/2015 | Papadopoulos et al. | |
| 2015/0210769 A1 | 7/2015 | Freeman et al. | |
| 2019/0010232 A1 | 1/2019 | Kalos et al. | |
| 2019/0284299 A1 | 9/2019 | Liu et al. | |
| 2020/0299412 A1 | 9/2020 | Liu et al. | |
| 2021/0032343 A1 | 2/2021 | Liu et al. | |
| 2021/0040193 A1 | 2/2021 | Yang et al. | |
| 2021/0230277 A1 | 7/2021 | Liu et al. | |

FOREIGN PATENT DOCUMENTS

| | | | |
|---|---|---|---|
| CN | 103429620 A | 12/2013 | |
| CN | 104080811 A | 10/2014 | |
| CN | 104114579 A | 10/2014 | |
| CN | 104520320 A | 4/2015 | |

(Continued)

OTHER PUBLICATIONS

Gunasekaran K. et al., Enhancing Antibody Fc Heterodimer Formation Through Electrostatic Steering Effects: Applications to Bispecific Molecules and Monovalent IgG . J Biol Chem., Apr. 16, 2010, vol. 285, No. 25, pp. 19637-19646 (10 Pages).

(Continued)

Primary Examiner — Lei Yao
(74) Attorney, Agent, or Firm — Sughrue Mion, PLLC

(57) ABSTRACT

Provided are an anti-PD-1/anti-HER2 natural antibody structural heterodimeric bispecific antibody and a method of preparing the same. Specifically, provided are a highly stable anti-PD-1/anti-HER2 heterodimeric bispecific antibody having characteristics of a natural IgG and having no mismatched heavy chain and light chain, and a method of preparing the same. The bispecific antibody may bind to both of two kinds of target molecules, and thus may be more effective in treating complex diseases.

9 Claims, 15 Drawing Sheets

Specification includes a Sequence Listing.

(56) References Cited

FOREIGN PATENT DOCUMENTS

| | | | |
|---|---|---|---|
| CN | 105111314 A | | 12/2015 |
| CN | 105175545 A | | 12/2015 |
| CN | 105828837 | * | 8/2016 |
| CN | 105828837 A | | 8/2016 |
| CN | 106883297 A | | 6/2017 |
| CN | 107325184 A | | 11/2017 |
| EP | 3 533 804 A1 | | 9/2019 |
| JP | 2010-530753 A | | 9/2010 |
| JP | 2014-530891 A | | 11/2014 |
| JP | 2014-533243 A | | 12/2014 |
| JP | 2016-508117 A | | 3/2016 |
| WO | 96/27011 A1 | | 9/1996 |
| WO | 2009/089004 A1 | | 7/2009 |
| WO | 2010/121766 A1 | | 10/2010 |
| WO | 2011/063348 A1 | | 5/2011 |
| WO | 2012/058768 A1 | | 5/2012 |
| WO | 2012/131555 A2 | | 10/2012 |
| WO | 2012/145493 A1 | | 10/2012 |
| WO | 2013/060867 A2 | | 5/2013 |
| WO | 2013/063702 A1 | | 5/2013 |
| WO | 2013/157953 A1 | | 10/2013 |
| WO | 2013/157954 A1 | | 10/2013 |
| WO | 2014/049003 A1 | | 4/2014 |
| WO | 2014/067011 A1 | | 5/2014 |
| WO | 2014/087248 A2 | | 6/2014 |
| WO | WO2015095418 | * | 5/2015 |
| WO | 2015/095404 A2 | | 6/2015 |
| WO | 2015/095412 A1 | | 6/2015 |
| WO | 2015/095418 A1 | | 6/2015 |
| WO | WO2015095412 | * | 6/2015 |
| WO | 2016/024021 A1 | | 2/2016 |
| WO | 2016/057933 A1 | | 4/2016 |
| WO | 2016/109415 A1 | | 7/2016 |
| WO | 2016/115274 A1 | | 7/2016 |
| WO | 2016/170039 A1 | | 10/2016 |
| WO | 2016/201051 A1 | | 12/2016 |
| WO | 2017/101828 A1 | | 6/2017 |
| WO | 2017/117179 A1 | | 7/2017 |
| WO | 2017/167919 A1 | | 10/2017 |
| WO | 2018/002339 A1 | | 1/2018 |
| WO | 2018/068336 A1 | | 4/2018 |
| WO | 2018059502 A1 | | 4/2018 |
| WO | 2019/068302 A1 | | 4/2019 |

OTHER PUBLICATIONS

Hye-Ji Choi, et al., "Engineering of Immunoglobulin Fc Heterodimers Using Yeast Surface-Displayed Combinatorial Fc Library Screening", PLOS One, Dec. 16, 2015, vol. 10, No. 12.
Sara Pilotto, et al., "Immune Checkpoint Inhibitors for Non-small-cell Lung Cancer: Does that Represent a 'New Frontier'?", Anti-Cancer Agent in Medicinal Chemistry, 2015, 7 pages, vol. 15, No. 0.
Elena Gianchecci, et al., "Recent insights into the role of the PD-1/PD-L1 pathway in immunological tolerance and autoimmunity", Autoimmunity Reviews, 2013, pp. 1091-1100, vol. 12.
Ashley Mentlik James, et al., "Combination immune therapies to enhance anti-tumor responses by NK cells", Frontiers in Immunology, Dec. 23, 2013, 12 pages, vol. 4, Art. 481.
Cornelia Haas, et al., "Mode of cytotoxic action of T cell-engaging BiTE antibody MT110", Immunobiology, 2009, pp. 441-453, vol. 214.
Sehar Afreen, et al., "The immunoinhibitory B7 H1 molecule as a potential target in cancer: Killing many birds with one stone", Hematol Oncol Stem Cell, First Quarter 2014, 17 pages, vol. 7, No. 1.
Greg T. Motz, et al., "Deciphering and Reversing Tumor Immune Suppression", Immunity Review, Jul. 25, 2013, pp. 61-73, vol. 39.
Michael A. Postow, et al., "Immune Checkpoint Blockade in Cancer Therapy", Journal of Clinical Oncology, Jun. 10, 2015, pp. 1974-1982, vol. 33, No. 17.
Michael Jager, et al., Immunomonitoring Results of a Phase II/III Study of Malignant Ascites Patients Treated with the Trifunctional Antibody Catumaxomab (Anti-EpCAM) x Anti-CD3), Cancer Research, Jan. 1, 2012, pp. 24-32, vol. 72, No. 1.
Anja Loffler, et al., "A recombinant bispecific single-chain antibody, CD19 X CD3, induces rapid and high Lymphoma-directed cytotoxicity by unstimulated T lymphocytes", Blood, Mar. 15, 2000, pp. 2098-2103, vol. 95, No. 6.
Drew M. Pardoll, "The blockade of immune checkpoints in cancer immunotherapy", Nature, Apr. 2012, pp. 252-264, vol. 12.
F. Revillion, et al., "ERBB2 Oncogene in Human Breast Cancer and its Clinical Significance", European Journal of Cancer, 1998, pp. 791-808, vol. 34, No. 6.
Dennis J. Slamon, et al., "Human Breast Cancer: Correlation of Relapse and Survival with Amplification of the HER-2/neu Oncogene", Science, Jan. 9, 1987, pp. 177-182, vol. 235.
DJ Slamon, et al., "Use of chemotherapy plus a monoclonal antibody against HER2 for metastatic breast cancer that overexpresses HER2", New England Journal of Medicine, Mar. 15, 2001, 4 pages, 783-792, vol. 344, No. 11.
Kim C. Ohaegbulam, et al., "Human cancer immunotherapy with antibodies to the PD-1 and PD-L1 pathway", Trends Mol Med, Jan. 2015, 23 pages, vol. 21, No. 1.
Christopher Wright, et al., "Expression of c-erbB-2 Oncoprotein: A Prognostic Indicator in Human Breast Cancer", Cancer Research, Apr. 15, 1989, pp. 2087-2090, vol. 49.
International Search Report for PCT/CN2017/111310 dated Feb. 22, 2018 [PCT/ISA/210].
Hye-Ji Choi, et al., "A Heterodimeric Fc-Based Bispecific Antibody Simultaneously Targeting VEGFR-2 and Met Exhibits Potent Antitumor Activity", Molecular Cancer Therapeutics, Oct. 16, 2013, vol. 12, No. 12, pp. 2748-2759 (14 pages total).
Camilla De Nardis et al., "A new approach for generating bispecific antibodies based on a common light chain format and the stable architecture of human immunoglobulin G1", J. Biol. Chem., 2017, vol. 292, No. 35, pp. 14706-14717 (13 pages total).
Ecuadorean Intellectual Property Office; Communication dated Oct. 8, 2019 issued in counterpart application No. SENADI-2019-22190.
International Search Report for PCT/CN2017/104044 dated Jan. 8, 2018 [PCT/ISA/210].
Pyzik, Michal, et al.,"FcRn: The Architect Behind the Immune and Nonimmune Functions of IgG and Albumin", The Journal of Immunology, vol. 194, 2015, pp. 4595-4603 (10 pages).
Roopenian, Derry, et al., "FcRn: the neonatal Fc receptor comes of age", Nature Reviews Immunology, vol. 7, 2007, pp. 715-725.
Sockolosky, Jonathan, et al., "The neonatal Fc receptor, FcRn, as a target for drug delivery and therapy", Advanced Drug Delivery Reviews, 2014, pp. 1-16.
Stapleton, Nigel, et al., "The multiple facets of FcRn in immunity", Immunological Reviews, 2015, vol. 268, pp. 253-268.
Ward, Sally, et al., "Targeting FcRn for the modulation of antibody dynamics", Molecular Immunology, 2015, pp. 1-11.
Written Opinion for PCT/CN2017/104044 dated Jan. 8, 2018 [PCT/ISA/237].
Atwell et al., "Stable Heterodimers from Remodeling the Domain Interface of a Homodimer using a Phage Display Library", J. Mol. Biol., 1997, vol. 270, pp. 26-35 (10 pages total).
International Search Report for PCT/IB2019/051008 dated May 29, 2019 [PCT/ISA/210].
Written Opinion for PCT/IB2019/051008 dated May 29, 2019 [PCT/ISA/237].
International Search Report for PCT/CN2018/118800 dated Mar. 4, 2019 [PCT/ISA/210].
Liu Boning, "Construction and anti-tumor effects of a new novel bispecific fusion protein targeting pd-L1 and cd47", South China University of Technology, 122 pages (2016).
Sockolosky et al., "Durable antitumor responses to CD47 blockade require adaptive immune stimulation", PNAS, 113(19): E2646-E2654 (2016).
Von Kreudenstein et al., "Improving biophysical properties of a bispecific antibody scaffold to aid developability", mAbs, 5(5): 646-654 (2013).

(56) References Cited

OTHER PUBLICATIONS

Brekken et al., "Selective inhibition of Vascular Endothelial Growth Factor (VEGF) Receptor 2 (KDR/Flk-1) Activity by a Monoclonal Anti-VEGF Antibody Blocks Tumor Growth in Mice", Cancer Research, 60, Sep. 15, 2000, pp. 5117-5124.
Bruns et al., "Effect of the Vascular Endothelial Growth Factor Receptor-2 Antibody DC101 Plus Gemcitabine on Growth, Metastasis and Angiogenesis of Human Pancreatic Cancer Growth Orthoropically in Nude Mice", Int. J. Cancer, 2002, 102, pp. 101-108.
Chen et al., "Molecular Pathways: Next Generation Immunotherapy—Inhibiting Programmed Death-Ligand 1 and Programmed Death-1", Clin. Cancer Res., Dec. 15, 2012, 18(24), pp. 6580-6587, 9 pages.
Ferrara et al., "The Biology of VEGF and its Receptors", Angiogenesis Focus, Nature Medicine, vol. 9 No. 6, Jun. 2003, pp. 669-676.
Folkman, J., "Clinical Applications of Research on Angiogenesis", New England Journal of Medicine, Seminars in Medicine of the Beth Israel Hospital, Boston, vol. 333, No. 26, Dec. 28, 1995, pp. 1757-1763.
Folkman, J., "Angiogenesis: An Organizing Principle for Drug Discovery?", Nature Reviews, Drug Discovery, vol. 6, Apr. 2007, pp. 273-286.
Gasparini et al., "Clinical Importance of the Determination of Tumor Angiogenesis in Breast Carcinoma: Much More Than a New Prognostic Tool", Journal of Clinical Oncology, vol. 13, No. 3, Mar. 1995, pp. 765-782.
Gianchecchi et al., "Recent Insights into the Role of the PD-1/PD-L1 Pathway in Immunological Tolerance and Autoimmunity", Autoimmunity Reviews 12 (2013), pp. 1091-1100.
Henick et al., "The PD-1 Pathway as a Therapeutic Target to Overcome Immune Escape Mechanisms in Cancer" Expert Opin. Ther. Targets, (2014), 18(12), 14 pages.
Johnson et al., "Randomized Phase II Trial Comparing Bevacizumab Plus Carboplatin and Paclitaxel With Carboplatin and Paclitaxel Alone in Previously Untreated Locally Advanced or Metastatic Non-Small-Cell Lung Cancer", Journal of Clinical Oncology, vol. 22, No. 11, Jun. 1, 2004, pp. 2184-2191.
Kabbinavar et al., "Phase II, Randomized Trial Comparing Bevacizumab Plus Fluorouracil (FU)/Leucovorin (LV) With FU/LV Alone in Patients with Metastatic Colorectal Cancer", J. Clin. Oncol., vol. 21, No. 1, Jan. 1, 2003, pp. 60-65.
Kim et al., "Prospects for Targeting PD-1 and PD-L1 in Various Tumor Types", Oncology Journal, Nov. 11, 2014 vol. 28, Issue 11, 12 pages.
Kumar et al., "Breast Carcinoma: Vascular Density Determined Using CD105 Antibody Correlates with Tumor Prognosis", Cancer Research, 59, Feb. 15, 1999, pp. 856-861.
Liu et al., "Fc Engineering for Developing Therapeutic Bispecific Antibodies and Novel Scaffolds", Frontiers in Immunology, Jan. 2017, vol. 8, Article 38, 15 pages.
Mellman, I., "The Renaissance of Immunotherapy is a Revolution for Cancer Patients", ASCO, GU 2015, 29 pages.
Mentlik-James et al., "Combination Immune Therapies to Enhance Anti-tumor Responses by NK Cells", Frontiers in Immunology, Dec. 23, 2013, vol. 4, Article 481, 13 pages.
Motz et al., "Deciphering and Reversing Tumor Immune Suppression", Immunity 39, Jul. 25, 2013, pp. 61-73.
Ohaegbulam et al., "Human Cancer Immunotherapy with Antibodies to the PD-1 and PD-L1 Pathway", Trends in Molecular Medicine, Jan. 2015, vol. 21, No. 1, pp. 24-33.
Pardoll, D., "The Blockade of Immune Checkpoints in Cancer Immunotherapy", Nature, Apr. 2012, vol. 12(4), pp. 252-264.
Pilotto et al., "Immune Checkpoint Inhibitors for Non-small-cell Lung Cancer: Does that Represent a New Frontier?", Anti-Cancer Agents in Medicinal Chemistry, 2015, vol. 15, No. 3, 7 pages.
Postow et al., "Immune Checkpoint Blockade in Cancer Therapy", Journal of Clinical Oncology, vol. 33, No. 17, Jun. 10, 2015, pp. 1974-1982 (10 pages).
Shaheen et al., "Inhibited Growth of Colon Cancer Carcinomatosis by Antibodies to Vascular Endothelial and Epidermal Growth Factor Receptors", British Journal of Cancer, (2001), 85(4), pp. 584-589.
Tartour et al., "Angiogenesis and Immunity: A Bidirectional Link Potentially Relevant for the Monitoring of Antiangiogenic Therapy and the Development of Novel Therapeutic Combination with Immunotherapy", Cancer Metastasis Rev., (2011), 30, pp. 83-95.
Tischer et al., "The Human Gene for Vascular Endothelial Growth Factor", The Journal of Biological Chemistry, vol. 266, No. 18, Jun. 25, 1991, pp. 11947-11954.
Yasuda et al., "Simultaneous Blockade of Programmed Death 1 and Vascular Endothelial Growth Factor Receptor 2 (VEGFR2) Induces Synergistic Anti-tumour Effect In Vivo", British Society for Immunology, Clinical and Experimental Immunology, 2013, 172, pp. 500-506.
International Search Report and Written Opinion for International Application PCT/CN2019/074541, dated Apr. 30, 2019, 24 pages.
"IMGT/2Dstructure-DB card for INN 9798", © Copyright 1995-2015 IMGT © [online], [archived on Apr. 25, 2015], Retrieved from the Internet: <URL: www.imgt.org/3Dstructure-DB/cgi/details.Ggi?pdbcode=9798>, (2015), 2 pgs.
International Search Report dated Jun. 21, 2018 in International Application No. PCT/CN2018/080858.
Written Opinion dated Jun. 21, 2018 in International Application No. PCT/CN2018/080858.
Chen, Lieping, et al., "Anti-PD-1/PD-L1 therapy of human cancer: past, present, and future", The Journal of Clinical Investigation, 125(9), (Sep. 2015), 3384-3391.
Extended European Search Report dated Dec. 7, 2020 in European Application No. 18777419.5.
Brinkmann, Ulrich, "The making of bispecific antibodies", MABS, vol. 9, No. 2, (Jan. 10, 2017), 182-212.
Ha, Ji-Hee, "Immunoglobulin Fc Heterodimer Platform Technology: From Design to Applications in Therapeutic Antibodies and Proteins", Frontiers in Immunology, vol. 7, (Oct. 6, 2016), 1-16.
Hartkopf, Andreas D., et al., "PD-1 and PDL1 immune Checkpoint Blockade to Treat Breast Cancer", Breast Care, vol. 11, No. 6, (Jan. 1, 2016), 385-390.

* cited by examiner

1. MIXTURE OF ANTI-HER2 AND ANTI-PD-1 HALF ANTIBODY MOLECULES
2. MIXTURE OF ANTI-HER2 AND ANTI-PD-1 HALF ANTIBODY MOLECULES AFTER OXIDATION
M: MOLECULAR WEIGHT MARKER

1. MOLECULAR WEIGHT MARKER
2. PURIFIED HETERODIMERIC ANTIBODY MOLECULE

SEQUENCE LISTING

<160> NUMBER OF SEQ ID NOS: 19

<210> SEQ ID NO 1
<211> LENGTH: 321
<212> TYPE: DNA
<213> ORGANISM: Artificial sequence
<220> FEATURE:
<223> OTHER INFORMATION: a nucleotide sequence of the light chain variable region

<400> SEQUENCE: 1

```
gacattcaga tgactcagag cccttcttca ctgtcagctt ccgtgggcga cagagtcact      60
atcacctgcc gcgcaagtca ggatgtgaac accgcagtcg cctggtacca gcagaagcct     120
ggcaaagctc caaagctgct gatctacagc gcatctttcc tgtattctgg agtgcccagt     180
aggtttagtg ggtcacggtc cggtaccgac ttcacactga ctatctccag cctgcagcct     240
gaggattttg ccacatacta ttgccagcag cactatacca cccccctac tttcggccag      300
ggaaccaaag tggagatcaa g                                               321
```

<210> SEQ ID NO 2
<211> LENGTH: 107
<212> TYPE: PRT
<213> ORGANISM: Artificial sequence
<220> FEATURE:
<223> OTHER INFORMATION: an amino acid sequence of the light chain
      variable region

<400> SEQUENCE: 2

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys
            100                 105
```

<210> SEQ ID NO 3
<211> LENGTH: 321
<212> TYPE: DNA
<213> ORGANISM: Artificial sequence
<220> FEATURE:
<223> OTHER INFORMATION: a nucleotide sequence of the light chain
      constant region

<400> SEQUENCE: 3

```
cgaactgtgg ccgctccaag cgtcttcatt tttccaccct ctgacgaaca gctgaagtca      60
gggacagctt ccgtggtctg tctgctgaac aattttttacc ccaggaggc caaagtgcag     120
tggaaggtcg ataacgctct gcagagcgga aattctcagg agagtgtgac agaacaggac     180
tcaaaagatt ccacttatag cctgtctagt accctgacac tgtccaaggc agactacgaa     240
aagcataaag tgtatgcctg tgaggtcaca catcagggtc tgtcaagccc cgtcactaag     300
tccttcaatc gtggcgaatg c                                               321
```

<210> SEQ ID NO 4
<211> LENGTH: 107
<212> TYPE: PRT
<213> ORGANISM: Artificial sequence
<220> FEATURE:
<223> OTHER INFORMATION: an amino acid sequence of the light chain
      constant region

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 360
<212> TYPE: DNA
<213> ORGANISM: Artificial sequence
<220> FEATURE:
<223> OTHER INFORMATION: a nucleotide sequence of the heavy chain
      variable region

<400> SEQUENCE: 5
gaggtgcagc tggtcgaaag tggggtggg ctggtgcagc caggcggatc actgaggctg      60
tcctgcgccg ctagcggctt caacatcaaa gacaccttata ttcactgggt ccgacaggca    120
ccagggaagg gtctggaatg ggtggctcgt atctacccta caaatggtta cactagatat    180
gccgactccg tgaaaggccg gtttactatt tctgctgata ccagtaagaa cacagcatac    240
ctgcagatga atagcctgag ggctgaggat accgcagtgt actattgctc tcggtggggg    300
ggtgacggct ctacgctat ggattattgg ggccagggaa ctctggtcac cgtgtccagc     360

<210> SEQ ID NO 6
<211> LENGTH: 120
<212> TYPE: PRT
<213> ORGANISM: Artificial sequence
<220> FEATURE:
<223> OTHER INFORMATION: an amino acid sequence of the heavy chain
      variable region

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 7
<211> LENGTH: 990
<212> TYPE: DNA
<213> ORGANISM: Artificial sequence
<220> FEATURE:
<223> OTHER INFORMATION: a nucleotide sequence of the heavy chain
      constant region

<400> SEQUENCE: 7

```
gcttcaacaa aaggaccttc cgtgtttcca ctggcaccct ctagtaagag tacttcagga      60
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaacca    300
aaaagctgtg ataagactca tacctgccca ccttgtcctg caccagagct gctgggaggt    360
ccaagcgtgt tcctgtttcc acccaagccc aaagacacac tgatgatttc tcgcacaccc    420
gaagtcactt gtgtggtcgt ggacgtgtcc cacgaggatc ctgaagtcaa gttcaactgg    480
tacgtggatg gcgtcgaggt gcataatgct aagaccaaac ccagagagga acagtacaac    540
agcacctatc gcgtcgtgtc tgtcctgaca gtgctgcacc aggattggct gaacggaaag    600
gagtacaagt gcaaagtgag caacaaggcc ctgcccgctc ctatcgagaa gaccatttct    660
aaggctaaag gccagcctag agaaccacag gtgtatacag agcctccaag tcgcgacgag    720
ctgacaaaaa accaggtctc cctgacttgt ctggtgaagg gattctaccc tagcgatatc    780
gcagtggagt gggaatctaa tgggcagcca gaaaacaatt ataagaccac accccctgtg    840
ctggactcag atggttcctt ctttctgctg agtgtgctga ccgtggacaa gtccaggtgg    900
cagcagggga acgtcttttc ctgcagcgtg atgcatgagg ccctgcacaa tcattacaca    960
cagaaatctc tgagtctgtc accaggaaag                                     990
```

<210> SEQ ID NO 8
<211> LENGTH: 330
<212> TYPE: PRT
<213> ORGANISM: Artificial sequence
<220> FEATURE:
<223> OTHER INFORMATION: an amino acid sequence of the heavy chain
      constant region

<400> SEQUENCE: 8

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
                115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Glu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Leu Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 333
<212> TYPE: DNA
<213> ORGANISM: Artificial sequence
<220> FEATURE:
<223> OTHER INFORMATION: an amino acid sequence of the light chain
      variable region

<400> SEQUENCE: 9
gagatcgtgc tgacccagag ccctgccaca ctgagcctga gccctggcga aagggccacc      60
ctgagctgca gggctagcaa gggcgtgagc accagcggct acagctacct gcactggtat     120
caacagaagc ccggccaggc tcctaggctg ctgatctacc tggccagcta tctggagagc     180
ggcgtgcccg ctagattcag cggaagcggc agcggcaccg acttcaccct gaccatcagc     240
agcctggagc ccgaggactt cgccgtgtac tactgccagc acagcaggga cctgcctctg     300
accttcggag gcggcaccaa ggtggagatc aag                                  333

<210> SEQ ID NO 10
<211> LENGTH: 111
<212> TYPE: PRT
<213> ORGANISM: Artificial sequence
<220> FEATURE:
<223> OTHER INFORMATION: an amino acid sequence of the light chain
      variable region

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
```

```
            20                  25                  30
Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110
```

<210> SEQ ID NO 11
<211> LENGTH: 360
<212> TYPE: DNA
<213> ORGANISM: Artificial sequence
<220> FEATURE:
<223> OTHER INFORMATION: a nucleotide sequence of the heavy chain
      variable region

<400> SEQUENCE: 11

```
caggtgcagc tggtgcagag cggcgtggag gtgaagaagc ctggcgccag cgtgaaggtg      60
agctgcaagg ccagcggcta cacccttcacc aactactaca tgtactgggt gaggcaggcc    120
cctggccaag gactggagtg gatgggcggc atcaaccccca gcaacggcgg caccaacttc    180
aacgagaagt tcaagaacag ggtgacccttg accaccgaca gcagcaccac caccgcctac    240
atggagctga gagcctgca gttcgacgac accgccgtgt actactgcgc caggagggac       300
tacaggttcg acatgggctt cgactactgg ggccagggca ccacagtgac cgtgtccagc     360
```

<210> SEQ ID NO 12
<211> LENGTH: 120
<212> TYPE: PRT
<213> ORGANISM: Artificial sequence
<220> FEATURE:
<223> OTHER INFORMATION: an amino acid sequence of the heavy chain
      variable region

<400> SEQUENCE: 12

```
Gln Val Gln Leu Val Gln Ser Gly Val Glu Val Lys Lys Pro Gly Ala
 1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
            115                 120
```

<210> SEQ ID NO 13
<211> LENGTH: 990
<212> TYPE: DNA

<213> ORGANISM: Artificial sequence
<220> FEATURE:
<223> OTHER INFORMATION: a nucleotide sequence of the heavy chain
      constant region

<400> SEQUENCE: 13

| gcttcaacaa | aaggaccttc | cgtgtttcca | ctggcaccct | ctagtaagag | tacttcagga | 60 |
| ggaaccgcag | cactgggatg | tctggtgaag | gactacttcc | cagagcccgt | caccgtgtct | 120 |
| tggaacagtg | gagcactgac | ctccggggtc | catacatttc | ctgccgtgct | gcagtcatcc | 180 |
| ggtctgtata | gcctgagctc | tgtggtcaca | gtcccaagtt | catccctggg | cacccagaca | 240 |
| tacatctgca | acgtgaatca | caaaccttcc | aatactaagg | tcgacaagaa | agtggaacca | 300 |
| aaaagctgtg | ataagactca | tacctgccca | ccttgtcctg | caccagagct | gctgggaggt | 360 |
| ccaagcgtgt | tcctgtttcc | acccaagccc | aaagacacac | tgatgatttc | tcgcacaccc | 420 |
| gaagtcactt | gtgtggtcgt | ggacgtgtcc | cacgaggatc | ctgaagtcaa | gttcaactgg | 480 |
| tacgtggatg | gcgtcgaggt | gcataatgct | aagaccaaac | cagagagga | acagtacaac | 540 |
| agcacctatc | gcgtcgtgtc | tgtcctgaca | gtgctgcacc | aggattggct | gaacggaaag | 600 |
| gagtacaagt | gcaaagtgag | caacaaggcc | ctgcccgctc | ctatcgagaa | gaccatttct | 660 |
| aaggctaaag | gccagcctag | agaaccacag | gtgtatacac | tgcctccaag | tcgcgacgag | 720 |
| ctgacaaaaa | accaggtctc | cctgctgtgt | ctggtgaagg | gattctaccc | tagcgatatc | 780 |
| gcagtggagt | gggaatctaa | tgggcagcca | gaaaacaatt | ataagaccac | accccctgtg | 840 |
| ctgcggtcag | atggttcctt | ctttctgtac | agtaaactga | ccgtggacaa | gtccaggtgg | 900 |
| cagcagggga | acgtctttc | ctgcagcgtg | atgcatgagg | ccctgcacaa | tcattacaca | 960 |
| cagaaatctc | tgagtctgtc | accaggaaag | | | | 990 |

<210> SEQ ID NO 14
<211> LENGTH: 330
<212> TYPE: PRT
<213> ORGANISM: Artificial sequence
<220> FEATURE:
<223> OTHER INFORMATION: an amino acid sequence of the heavy chain
      constant region

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Arg Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 321
<212> TYPE: DNA
<213> ORGANISM: Artificial sequence
<220> FEATURE:
<223> OTHER INFORMATION: a nucleotide sequence of the light chain
      variable region

<400> SEQUENCE: 15
gatatcgttc tcacccagtc tccagccacc ctgtctgtga ctccaggaga tagcgtcagt     60
ctttcctgca gggccaacca agtattagc aacaacctac actggtatca acaaagatca    120
catgagtctc cgaggcttct catcagattt gcttcccagt ccatctctgg atcccctcc    180 aggttcagtg gcagtggatc aggacagat tcactctca gtatcaacag tgtggagact    240
gaagattttg aatgtattt ctgtcaacag agtgacaact ggcctctcac gttcggtgct    300
gggaccaagc tggagatcaa g                                             321

<210> SEQ ID NO 16
<211> LENGTH: 107
<212> TYPE: PRT
<213> ORGANISM: Artificial sequence
<220> FEATURE:
<223> OTHER INFORMATION: an amino acid sequence of the light chain
      variable region

<400> SEQUENCE: 16

Asp Ile Val Leu Thr Gln Ser Pro Ala Thr Leu Ser Val Thr Pro Gly
1               5                   10                  15

Asp Ser Val Ser Leu Ser Cys Arg Ala Asn Gln Ser Ile Ser Asn Asn
            20                  25                  30

Leu His Trp Tyr Gln Gln Arg Ser His Glu Ser Pro Arg Leu Leu Ile
            35                  40                  45

```
Arg Phe Ala Ser Gln Ser Ile Ser Gly Ile Pro Ser Arg Phe Ser Gly
    50                  55                  60
Ser Gly Ser Gly Thr Asp Phe Thr Leu Ser Ile Asn Ser Val Glu Thr
 65                 70                  75                  80
Glu Asp Phe Gly Met Tyr Phe Cys Gln Gln Ser Asp Asn Trp Pro Leu
                 85                  90                  95
Thr Phe Gly Ala Gly Thr Lys Leu Glu Ile Lys
            100                 105
```

<210> SEQ ID NO 17
<211> LENGTH: 351
<212> TYPE: DNA
<213> ORGANISM: Artificial sequence
<220> FEATURE:
<223> OTHER INFORMATION: a nucleotide sequence of the heavy chain
      variable region

<400> SEQUENCE: 17

```
gaggttcagc tgcaggagtc tggggagggc ttagtgaagc ctggagggtc cctgaaactc    60
tcctgtgcag cctctggatt cactttcagt agctatggca tgtcttgggt tcgccagact   120
ccggagaaga ggctggagtg ggtcgcaagc attagtggtg gtggtcgtta tacctactat   180
ccagacagta tgaagggccg attcaccatc tccagagaca atgccaagaa caacctgcac   240
ctgcaaatga gcagtctgag gtctgaggac acggccttgt attactgtgt ctatgaatat   300
ttttatacta tggactactg gggtcaagga acctcagtca ccgtctcctc a            351
```

<210> SEQ ID NO 18
<211> LENGTH: 117
<212> TYPE: PRT
<213> ORGANISM: artificial sequence
<220> FEATURE:
<223> OTHER INFORMATION: an amino acid sequence of the heavy chain
      variable region

<400> SEQUENCE: 18

```
Glu Val Gln Leu Gln Glu Ser Gly Gly Gly Leu Val Lys Pro Gly Gly
  1               5                  10                  15
Ser Leu Lys Leu Ser Cys Ala Ala Ser Gly Phe Thr Phe Ser Ser Tyr
             20                  25                  30
Gly Met Ser Trp Val Arg Gln Thr Pro Glu Lys Arg Leu Glu Trp Val
         35                  40                  45
Ala Ser Ile Ser Gly Gly Gly Arg Tyr Thr Tyr Tyr Pro Asp Ser Met
     50                  55                  60
Lys Gly Arg Phe Thr Ile Ser Arg Asp Asn Ala Lys Asn Asn Leu His
 65                  70                 75                  80
Leu Gln Met Ser Ser Leu Arg Ser Glu Asp Thr Ala Leu Tyr Tyr Cys
                 85                  90                  95
Val Tyr Glu Tyr Phe Tyr Thr Met Asp Tyr Trp Gly Gln Gly Thr Ser
            100                 105                 110
Val Thr Val Ser Ser
        115
```

<210> SEQ ID NO 19
<211> LENGTH: 15
<212> TYPE: PRT
<213> ORGANISM: artificial sequence
<220> FEATURE:
<223> OTHER INFORMATION: linker

<400> SEQUENCE: 19

```
Gly Gly Gly Gly Ser Gly Gly Gly Gly Ser Gly Gly Gly Gly Ser
1               5                   10                  15
```

ANTI-PD-1/ANTI-HER2 NATURAL ANTIBODY STRUCTURAL HETERODIMERIC BISPECIFIC ANTIBODY AND METHOD OF PREPARING THE SAME

CROSS REFERENCE TO RELATED APPLICATIONS

This application is a National Stage of International Application No. PCT/CN2017/111310, filed on Nov. 16, 2017, which claims priority from China Patent Application No. 201611016435.0, filed on Nov. 18, 2016.

SEQUENCE LISTING

The content of the electronically submitted sequence listing, file name: Sequence_Listing_As_Filed.txt; size: 21,488 bytes; and date of creation: Nov. 4, 2021, filed herewith, is incorporated herein by reference in its entirety.

TECHNICAL FIELD

The present disclosure relates to an anti-PD-1/anti-HER2 natural antibody structural heterodimeric bispecific antibody and a method of preparing the same. Specifically, the present disclosure provides a highly stable anti-PD-1/anti-HER2 heterodimeric bispecific antibody having characteristics of a natural IgG and having no mismatched heavy chain and light chain, and a method of preparing the same.

BACKGROUND ART

Monoclonal antibodies are highly specific antibodies that act only on a single antigenic determinant and have been widely used for cancer, inflammation, autoimmune diseases, infectious diseases, etc. However, such therapeutic molecules do not exhibit sufficient pharmacological effects when used alone. This is attributed to the complexity of the diseases. For example, cancer or inflammatory diseases are often associated with interactions between molecular pathways and signaling pathways that mediate various diseases. In this case, a molecule having a single target may not provide an optimal therapeutic effect, and the therapeutic effect may be improved by simultaneously blocking molecules located on multiple targets or at many sites on a single target. At the same time, dual targeting therapy using multispecificity such as bispecific molecules may simplify the process of developing new drugs because a bispecific molecule is a single molecule. As compared with using a combination of several monospecific molecules, this method is a more convenient method for both patients and healthcare providers.

Many different types of bispecific antibodies or bifunctional molecules have been known in the art. The first bispecific antibody was obtained by coupling two IgG molecules, Fab', or (Fab')2 fragments using a chemical method and a bifunctional coupling reagent. However, such a chemically coupled bispecific antibody has many limitations, including the intensity of production work, purification of heterologous coupling products, complexity in the removal of homologous coupling products, original monospecific antibodies, or fragments, low efficiency, etc.

Another method used in the production of bispecific antibodies is to use a hybrid-hybridoma (quadroma) technology, which is a method of producing a bispecific antibody by somatic fusion of two kinds of hybridoma cell lines that secrete different antibodies. Due to arbitrary pairing of heavy and light chains of immunoglobulins, only one-tenth of the antibody mixture is the functional bispecific antibody required, thus complicating the purification process and reducing the production yield.

WO2013060867 describes a method of mass-producing a heterodimeric bispecific antibody. In this method, a mixture of two kinds of homodimeric antibodies is first reduced, and asymmetric amino acid mutations are introduced into CH3 domains of the two kinds of homodimeric antibodies to promote Fab arm exchange of the different antibodies, and inter-chain disulfide bonds of the hinge region are oxidized to form a stable bispecific antibody.

WO2009089004 describes a method of preparing a heterodimeric protein. In this method, amino acids at the CH3-CH3 interface are mutated into charged amino acids such that heterodimerization is electrostatically favorable but homodimer formation is electrostatically unfavorable.

U.S. Pat. No. 5,731,168 describes a method of preparing a heterodimeric IgG using a protuberance-into-cavity strategy. In this method, "protuberances" are constructed by replacing small amino acids at the interface of the CH3 domain of a first chain with larger amino acids, and at the same time, "cavities" are created by replacing corresponding large amino acids of the CH3 domain of a second chain with smaller amino acids. The protuberance and cavity interaction is favorable to heterodimeric IgG formation but unfavorable to homodimer formation.

WO2012058768 describes a method of preparing a highly specific stable heterodimeric IgG. This method combines both negative and positive design strategies along with structural and computational modeling guided protein engineering techniques to mutate a plurality of amino acids in the IgG1 CH3 structural domain, thereby forming a stable heterodimeric IgG with low homodimeric impurities.

Programmed death receptor-1 (PD-1) is an immune checkpoint that has recently attracted much attention, and is mainly involved in the control of T cell activation, and regulates strength and duration of immune responses. Under normal conditions, PD-1 mediates and maintains self-tolerance of body tissues and prevents damage of autologous tissue caused by excessive activation of the immune system during an inflammatory process, and therefore, has a positive effect on the prevention of autoimmune diseases. Under pathological conditions, PD-1 is involved in the occurrence and development of tumor immunity and various autoimmune diseases (Anticancer Agents Med Chem. 2015; 15(3): 307-13. Hematol Oncol Stem Cell Ther. 2014 March; 7(1): 1-17. Trends Mol Med. 2015 January; 21(1):24-33. Immunity. 2013 Jul. 25; 39(1):61-73. J Clin Oncol. 2015 Jun. 10; 33(17):1974-82.).

PD-1 belongs to the CD28 family, but unlike other members of the CD28 family such as CTLA4, etc., it may form covalent dimers via disulfide bonds, and exists in a monomeric form. The structure of PD-1 mainly includes an extracellular immunoglobulin variable region as a structural domain, a hydrophobic transmembrane domain, and an intracellular domain. The intracellular domain includes two independent phosphorylation sites. The phosphorylation sites are an immunoreceptor tyrosine-based inhibitory motif (ITIM) and an immunoreceptor tyrosine-based switch motif (ITSM). PD-1 is inducibly expressed on the surface of activated T cells, and also on B cells, NK cells, monocytes, and DC cells. PD-1 ligands include programmed death ligand 1 (PD-L1) and programmed death ligand 2 (PD-L2), and these ligands belong to the B7 family. Of them, PD-L1 is inducibly expressed on the surface of various immune cells including T cells, B cells, monocytes, macrophages, DC cells, endothelial cells, epidermal cells, etc., but PD-L2 is inducibly expressed only on some immune cells such as macrophages, DC cells, B cells, etc. (Autoimmun Rev, 2013, 12(11):1091-1100. Front Immunol, 2013, 4:481. Nat Rev Cancer, 2012, 12(4): 252-264. Trends Mol Med. 2015 January; 21(1): 24-33.).

In the 1980s, Dennis Slamon first discovered overexpression of the human epidermal growth factor receptor 2 (HER2) gene in 30% of 189 primary breast cancer cases, and revealed that HER2 is closely associated with overall survival rate and recurrence time (Salman D J, et al., Science, 235:177-182, 1985). According to recent studies, HER2 is overexpressed in approximately 25-30% of breast cancer patients (Revillion F et al., Eur J Cancer, 34:791-808, 1998), which is associated with malignant progression of tumors (Wright C et al., Cancer Res, 49: 2087-2090, 1989).

Trastuzumab is a humanized monoclonal antibody against the HER2 extracellular domain (Carter P et al., PNAS, 89(10):4285-4289, 1992). However, the anti-cancer effect of trastuzumab in clinical studies is often lower than that in preclinical studies, and therefore, trastuzumab is generally used in combination with chemotherapeutic agents (Slamon D J et al., N Engl J Med, 344:783-792, 2001).

Designing bi-functional antibodies capable of recruiting effector cells is an effective means of improving the efficacy of antibodies. Until now, most studies have been conducted to exploit the function of the CD3 molecule. A target tumor can be effectively removed through activation of killer T cells by the CD3 molecule (Haas C et al., Immunobiology, 214:441-453, 2009). Among them, BiTE, which is a recombinant bifunctional T cell-stimulating antibody developed by Micromet, Inc., has shown great promise, but the biggest problem is that its serum half-life is very short and its half-life in the human body is only 1 hour (Loffler A et al., Blood, 95:2098-2103). This is attributed to the structure of BiTE itself. BiTE is composed of two single-chain antibody fragments. Its molecular weight is a mere 60 kDa, and Fc fragments which play an important role in half-life extension in an antibody molecule are removed.

Catumaxomab is another type of promising multi-functional antibody, and is a hetero Ig molecule targeting CD3 and EpCAM. Currently, this product is approved for the treatment of malignant ascites (Jager M et al., Cancer Res, 72:24-32, 2012). Still another multifunctional antibody under phase II clinical trial is ertumaxomab which targets CD3 and HER2. A heavy chain and a light chain of the heteroantibody is derived from rat IgG and targets CD3; and another heavy chain and light chain is derived from mouse IgG and targets HER2. A problem which accompanies this is that production of these products is very difficult. To acquire clones expressing bifunctional ertumaxomab, one hybridoma expressing a CD3 antibody and one hybridoma expressing a HER2 antibody are first prepared, respectively, and then the two hybridomas are hybridized to obtain a quadroma which is a bifunctional antibody capable of expressing anti-CD3 and HER2. Usually, in order to produce a single-target antibody, only one hybridoma is needed. In comparison, the production process of the bifunctional antibody is much more complicated, and it is also more difficult to obtain the quadroma, which may result in extremely high immunogenicity due to its rat origin.

Further, the most obvious side effect of the anti-CD3 antibody is a transient burst of systemic cytokine release, also called a 'cytokine storm'. Accordingly, there is a demand for a new bifunctional antibody that recruits immune cells to the surface of tumor cells.

DESCRIPTION OF EMBODIMENTS

Technical Problem

A first aspect of the present disclosure relates to a heterodimeric bispecific antibody including a first antigen-binding functional domain capable of specifically binding to PD-1 and a second antigen-binding functional domain capable of specifically binding to HER2. The bispecific antibody may include a first Fc chain and a second Fc chain which are linked to each other via one or more disulfide bonds, wherein the first Fc chain and the second Fc chain are respectively linked to the PD-1 antigen-binding functional domain and the HER2 antigen-binding functional domain, and the first Fc chain and the second Fc chain include 5 amino acid substitutions at the following positions:

1) amino acid substitutions at positions 366 and 399 of the first Fc chain and amino acid substitutions at positions 351, 407, and 409 of the second Fc chain; or 2) amino acid substitutions at positions 366 and 409 of the first Fc chain and amino acid substitutions at positions 351, 399, and 407 of the second Fc chain, wherein the first and second Fc chains including the above amino acid substitutions respectively have a tendency to undergo heterodimerization rather than homodimerization, and the amino acid positions are numbered according to the Kabat EU numbering system.

In an embodiment, the amino acid substitutions of the first Fc chain and the second Fc chain are as follows:

a) substitution of glycine, tyrosine, valine, proline, aspartic acid, glutamic acid, lysine, or tryptophan at position 351;

b) substitution of leucine, proline, tryptophan, or valine at position 366;

c) substitution of cysteine, asparagine, isoleucine, glycine, arginine, threonine, or alanine at position 399;

d) substitution of leucine, alanine, proline, phenylalanine, threonine, or histidine at position 407; and e) substitution of cysteine, proline, serine, phenylalanine, valine, glutamine, or arginine at position 409.

In an embodiment, the amino acid substitutions may include:

a) T366L and D399R substitutions in the first Fc chain and L351E, Y407L, and K409V substitutions in the second Fc chain;

b) T366L and D399C substitutions in the first Fc chain and L351G, Y407L, and K409C substitutions in the second Fc chain;

c) T366L and D399C substitutions in the first Fc chain and L351Y, Y407A, and K409P substitutions in the second Fc chain;

d) T366P and D399N substitutions in the first Fc chain and L351V, Y407P, and K409S substitutions in the second Fc chain;

e) T366W and D399G substitutions in the first Fc chain and L351D, Y407P, and K409S substitutions in the second Fc chain;

f) T366P and D399I substitutions in the first Fc chain and L351P, Y407F, and K409F substitutions in the second Fc chain;

g) T366V and D399T substitutions in the first Fc chain and L351K, Y407T, and K409Q substitutions in the second Fc chain;

h) T366L and D399A substitutions in the first Fc chain and L351W, Y407H, and K409R substitutions in the second Fc chain.

In an embodiment, the amino acid substitutions may include:

a) T366L and K409V substitutions in the first Fc chain and L351E, Y407L, and D399R substitutions in the second Fc chain;

b) T366L and K409C substitutions in the first Fc chain and L351G, Y407L, and D399C substitutions in the second Fc chain;

c) T366L and K409P substitutions in the first Fc chain and L351Y, Y407A, and D399C substitutions in the second Fc chain;

d) T366P and K409S substitutions in the first Fc chain and L351V, Y407P, and D399N substitutions in the second Fc chain;

e) T366W and K409S substitutions in the first Fc chain and L351D, Y407P, and D399G substitutions in the second Fc chain;

f) T366P and K409F substitutions in the first Fc chain and L351P, Y407F, and D399I substitutions in the second Fc chain;

g) T366V and K409Q substitutions in the first Fc chain and L351K, Y407T, and D399T substitutions in the second Fc chain;

h) T366L and K409R substitutions in the first Fc chain and L351W, Y407H, and D399A substitutions in the second Fc chain.

In an embodiment, the first Fc chain has amino acid substitutions of T366L and D399R, and the second Fc chain has amino acid substitutions of L351E, Y407L, and K409V.

In an embodiment, the Fc chain is derived from IgG.

In an embodiment, the PD-1 and HER2 antigen-binding functional domains are Fab fragments or scFv fragments.

In an embodiment, the PD-1 and HER2 antigen-binding functional domains are all Fab fragments.

In an embodiment, one of the PD-1 and HER antigen-binding functional domains is a Fab fragment and the other is a scFv fragment.

In an embodiment, the Fab fragment may include a first heavy chain variable region and a second heavy chain variable region that are different form each other and a first light chain variable region and a second light chain variable region that are different from each other.

In an embodiment, an amino acid sequence of the bispecific antibody is selected from SEQ ID NOs: 2, 4, 6, 8, 10, 12, 14, 16, and 18.

A second aspect of the present disclosure relates to an isolated polynucleotide encoding the heterodimeric bispecific antibody described in the first aspect.

In an embodiment, a sequence of the polynucleotide is selected from SEQ ID NOs: 1, 3, 6, 7, 9, 13, 15, and 17.

A third aspect of the present disclosure relates to a recombinant plasmid including the isolated polynucleotide described in the second aspect.

In an embodiment, the expression vector is a plasmid vector X0GC which is obtained by modifying pcDNA.

A fourth aspect of the present disclosure relates to a host cell including the isolated polynucleotide described in the second aspect or the recombinant expression vector described in the third aspect.

In an embodiment, the host cell is selected from a human embryonic kidney cell HEK293, or HEK293T, HEK293F, or HEK293E derived from the HEK293 cell; and a Chinese hamster ovary cell CHO, or CHO-S, CHO-dhfr⁻, CHO/DG44, or ExpiCHO derived from CHO cell.

A fifth aspect of the present disclosure relates to a composition including the heterodimeric bispecific antibody described in the first aspect, the isolated polynucleotide described in the second aspect, the recombinant expression vector described in the third aspect, or the host cell described in the fourth aspect, and a pharmaceutically acceptable carrier.

A sixth aspect of the present disclosure relates to a method of producing the heterodimeric bispecific antibody described in the first aspect, the method including:

1) expressing the isolated polynucleotide described in the second aspect or the recombinant expression vector described in the third aspect in a host cell;

2) reducing each protein expressed in the host cell; and 3) mixing the reduced proteins and then oxidizing the mixture.

In an embodiment, the host cell is selected from a human embryonic kidney cell HEK293, or HEK293T, HEK293F, or HEK293E derived from the HEK293 cell; and a Chinese hamster ovary cell CHO, or CHO-S, CHO-dhfr⁻, CHO/DG44, or ExpiCHO derived from CHO cell.

In an embodiment, the reducing may include 1) adding a reducing agent, wherein the reducing agent is 2-mercaptoethylamine, dithiothreitol, tri(2-carboxyethyl)phosphine, other chemical derivatives, or a combination thereof, 2) performing a reduction reaction in the presence of dithiothreitol at a concentration of 0.1 mM or more at 4° C. for at least 3 hours, and 3) removing the reducing agent by desalting, etc.

In an embodiment, the oxidizing may include 1) oxidizing in air or adding an oxidizing agent, wherein the oxidizing agent is selected from L-dehydroascorbic acid and other chemical derivatives, and 2) performing an oxidization reaction in the presence of L-dehydroascorbic acid at a concentration of 0.5 mM or more at 4° C. for at least 5 hours.

In an embodiment, the method may further include isolating and purifying.

A seventh aspect of the present disclosure relates to use of the heterodimeric bispecific antibody described in the first aspect, and/or the isolated polynucleotide described in the second aspect, and/or the recombinant expression vector described in the third aspect, and/or the host cell described in the fourth aspect, and/or the composition described in the fifth aspect, in the preparation of a drug for preventing and/or treating a disease of a subject.

An eighth aspect of the present disclosure relates to use of the heterodimeric bispecific antibody described in the first aspect, and/or the isolated polynucleotide described in the second aspect, and/or the recombinant expression vector described in the third aspect, and/or the host cell described in the fourth aspect, and/or the composition described in the fifth aspect, in the prevention and/or treatment of a disease of a subject.

A ninth aspect of the present disclosure relates to a method of preventing and/or treating a disease, the method including administering the heterodimeric bispecific antibody described in the first aspect, and/or the isolated polynucleotide described in the second aspect, and/or the recombinant expression vector described in the third aspect, and/or the host cell described in the fourth aspect, and/or the composition described in the fifth aspect to a subject in need thereof.

In an embodiment, the subject may be a mammal, or preferably may be a human subject.

In an embodiment, the disease may be selected from tumors such as leukemia, lymphoma, myeloma, brain tumor, head and neck squamous cell carcinoma, non-small cell lung cancer, nasopharyngeal carcinoma, esophageal cancer, stomach cancer, pancreatic cancer, gallbladder cancer, liver cancer, colon cancer, breast cancer, ovarian cancer, cervical cancer, endometrial cancer, uterine sarcoma, prostate cancer, bladder cancer, renal cell carcinoma, and melanoma.

Advantageous Effects of Disclosure

In the present disclosure, a completely new anti-PD-1/anti-HER2 natural antibody structural heterodimeric bispecific antibody has been designed by employing PD-1 as a molecule recruiting immune cells and HER2 as a target molecule of tumor cells. The bispecific antibody is a highly stable anti-PD-1/anti-HER2 heterodimeric bispecific antibody having characteristics of a natural IgG and having no mismatched heavy chain and light chain. The bispecific antibody may bind to both of the two kinds of target molecules, PD-1 and HER-2, and thus may be more effective in treating complex diseases.

BRIEF DESCRIPTION OF DRAWINGS

FIG. 11A and FIG. 11B show HER2-binding activity and PD-1-binding activity of the anti-PD-1/anti-HER2 heterodimeric antibody molecule, wherein FIG. 11A and FIG. 11B show HER2-binding activity and PD-1-binding activity, respectively;

FIG. 13A and FIG. 13B show blocking activity of the anti-PD-1/anti-HER2 heterodimeric antibody molecule against PD-1/PD-L1 binding and PD-1/PD-L2 binding, wherein FIG. 13A and FIG. 13B show blocking activity against PD-1/PD-L1 and PD-1/PD-L2 binding, respectively;

BEST MODE

Definitions

Figure 1:
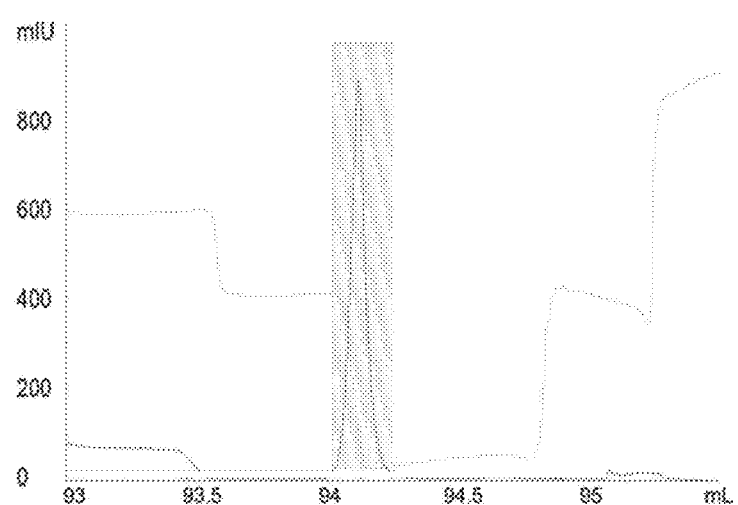
FIG. 1 shows an elution peak of a monomer of a heterodimeric antibody molecule.

Covalent linkage means that two Fc chains or any one Fc chain and an antigen-binding functional domain linked thereto in a heterodimeric bispecific antibody are linked with each other via a covalent bond to form a single molecule. Among them, the Fc chain includes a first antigen-binding functional domain and a second antigen-binding functional domain linked via one or more covalent bonds (or disulfide bond chains); the first Fc chain and the second Fc chain each is linked to one antigen-binding functional domain via a covalent bond (an imine bond or a peptide bond); and The antigen-binding functional domain is a domain in which a specific interaction with a target molecule such as an antigen occurs, and its action is highly selective, and a sequence that recognizes one target molecule generally does not recognize other molecule sequences. A representative antigen-binding functional domain includes an antibody variable region, a structural variant of the antibody variable region, a receptor binding domain, a ligand binding domain, or an enzyme binding domain.

The linkage via one or more disulfide bond chains refers to formation of a heterodimer fragment by a linkage between the first Fc chain and the second Fc chain via one or more disulfide bond chains. In the present disclosure, one or more disulfide bonds may be formed when the first Fc chain and the second Fc chain or the first Fc chain and the second Fc chain and the antigen-binding functional domains linked thereto are synthesized in the same cell, or may be formed by in vitro reduction after the first Fc chain and the second Fc chain or the first Fc chain and the second Fc chain and the antigen-binding functional domains linked thereto are synthesized in the different cells, respectively.

The first Fc chain and the second Fc chain constitutes a binding fragment via a covalent bond, and the covalent bond include a disulfide bond, and each chain includes at least a part of an immunoglobulin heavy chain constant region; the first chain and the second chain are different from each other in their amino acid sequences and include a different amino acid at least one position. In the first Fc chain and the second Fc chain of the present disclosure, a strong repulsive force exists between the same chains and an attractive force exists between the different chains. Therefore, the first Fc chain and the second Fc chain or the first Fc chain and the second Fc chain and the antigen-binding functional domains linked thereto have a tendency to undergo heterodimeric formation, when co-expressed in a cell. When the first Fc chain and the second Fc chain or the first Fc chain and the second Fc chain and the antigen-binding functional domains linked thereto are expressed in different two host cells, respectively, the first Fc chains, or the first Fc chain and the antigen-binding functional domain linked thereto have no tendency to undergo homodimeric formation, and the second Fc chains, or the second Fc chain and the antigen-binding functional domain linked thereto also have no tendency to undergo homodimeric formation. In the present disclosure, when the first Fc chain and the second Fc chain, or the first Fc chain and the second Fc chain and the antigen-binding functional domains linked thereto are expressed in two different host cells, respectively and a reducing agent is present, a percentage of homodimers is less than 50%, that is, a percentage of monomers (one Fc chain or one Fc chain and one antigen-binding functional domain linked thereto) is 50% or more.

An immunoglobulin has a symmetric structure having four polypeptide chains; two chains are identical heavy chains which are relatively long and have a relatively high molecular weight, each including 450 to 550 amino acid residues and having a relative molecular weight of 55000 Da to 70000 Da; and the other two chains are identical light chains (L chains) which are relatively short and have a relatively low molecular weight, each including 210 amino acid residues and having a relative molecular weight of about 24000 Da. About 110 amino acid sequences near the N-terminus of immunoglobulin heavy and light chains are highly variable, and the region is called a variable region (V region), and the rest amino acid sequences near the C-terminus thereof are relatively stable, called a constant region (C region). The variable region in the heavy chain occupies approximately ¼ of the length of the heavy chain, and the constant region occupies approximately ¾ of the length of the heavy chain. The known 5 types of immunoglobulins are IgG(γ), IgA(α), IgD(δ), IgM(μ) and IgE(ε). Among them, the former three kinds of immunoglobulins have three constant regions consisting of CH1, CH2 and C3 in H chain, and the latter two kinds of immunoglobulins (IgM and IgE) have one VH domain and four constant domains, i.e., CH1 to CH4 in H chain. The constant region is a framework of an immunoglobulin molecule, and is also one of regions activating immune responses.

A part of the constant region of the present disclosure includes at least an interaction region of the first Fc chain and the second Fc chain, and in the case of IgG, this region is located at any amino acid positions of CH3 domain and includes at least GLN347, TYR349, THR350, LEU351, SER354, ARG355, ASP356, GLU357, LYS360, SER364, THR366, LEU368, LYS370, ASN390, LYS392, THR394, PRO395, VAL397, ASP399, SER400, PHE405, TYR407, LYS409, LYS439.

The first Fc chain and the second Fc chain each linked to one antigen-binding functional domain via a covalent bond or a linker indicate the first Fc chain and the second Fc chain each linked to an antigen-binding fragment of one antibody, or a single chain antibody capable of recognizing an antigen, or other antibody fragment variant capable of recognizing an antigen, or a receptor capable of recognizing a ligand, or a ligand capable of recognizing a receptor via a covalent bond or a linker. The covalent bond is a kind of chemical bonding, in which two or more atoms together use their outer electrons, in the ideal case of electronic saturation, thus forming a relatively stable chemical structure, or the interaction between atoms is formed by shared electron pair. Atoms of the same element or atoms of different elements may be all linked via the covalent bond. The covalent bond of the first Fc chain and the second Fc chain of the present disclosure may include an amide bond formed by dehydration between an amino group of an amino acid of one molecule and a carboxyl group of an amino acid of another molecule, or an amide bond between an aldehyde group of ethylene glycol or polyethylene glycol or other compound or a polymer thereof and an amino group of an amino acid of one molecule, but is not limited thereto. The linker is one amino acid sequence or one compound or one multimer of the one compound capable of linking two polypeptide chains via a covalent bond. Among them, the one amino acid sequence may include, but is not limited to, a small peptide, such as GGGGSGGGGSGGGGS (SEQ ID NO: 19), and the amino acid sequence may link the first Fc chain or the second Fc chain and a single chain antibody capable of recognizing an antigen or other antibody fragment structural variant capable of recognizing an antigen via an amide bond.

The first Fc chain and the second Fc chain have a tendency to undergo heterodimeric formation and no tendency to undergo homodimeric formation, which means that in the first Fc chain and the second Fc chain, a strong repulsive force exists between the same polypeptide chains and an attractive force exists between the different polypeptide chains, and therefore, the first Fc chain and the second Fc chain or the first Fc chain and the second Fc chain and the antigen-binding functional domains linked thereto have a tendency to undergo heterodimeric formation, when co-expressed in a cell. When the first Fc chain and the second Fc chain or the first Fc chain and the second Fc chain and the antigen-binding functional domains linked thereto are expressed in two different host cells, respectively, the first Fc chains, or the first Fc chain and the antigen-binding functional domain linked thereto have no tendency to undergo homodimeric formation, and the second Fc chains, or the second Fc chain and the antigen-binding functional domain linked thereto also have no tendency to undergo homodimeric formation.

The Kabat EU numbering system means that Kabat assigns a number to each amino acid in an antibody sequence, and this method of assigning residue numbers has become standard in the field. The Kabat's method is extendible to other antibodies not included in his compendium by aligning a target antibody with one of the consensus sequences in Kabat by reference to conserved amino acids.

Fc fragment region refers to a fragment crystallizable (Fc) and corresponds to CH2 and CH3 structural domains of Ig, and is a fragment where an interaction between Ig and an effector molecule or a cell occurs.

IgG is an abbreviation for immunoglobulin G (IgG), and is the main type of antibody in the serum. Human IgG has four subclasses of IgG1, IgG2, IgG3, and IgG4 based on antigenic differences in r chains in the IgG molecule.

A half antibody molecule has a structure formed by one heavy chain and one light chain of an antibody, wherein the heavy chain and the light chain may be linked via a covalent bond, or has a monovalent antibody structure recognizing an antigen, which may be formed without a covalent bond.

Fab fragment is a molecule-recognizing sequence, and a fragment of antigen binding (Fab), and corresponds to two arms of an antibody molecule, each consisting of a complete light chain and VH and CH1 structural domains of a heavy chain. scFv is a molecule-recognizing sequence, and is a structural isomer of an antibody fragment obtained by genetic modification of a light chain variable region and a heavy chain variable region of an antibody. An extracellular domain of a membrane receptor is a molecule-recognizing sequence, and the membrane receptor usually includes an extracellular region that is located outside the cell and recognizes and binds to the corresponding antigen or ligand, a transmembrane region that anchors the receptor onto the cell surface, and an intracellular region that has intracellular kinase activity or a signaling pathway. The ligand of the cell membrane receptor refers to a protein, a small peptide, or a compound that may be recognized and bound by the extracellular region of the membrane receptor. Cytokines are low-molecular weight soluble proteins that are produced by various types of cells induced by immunogens, mitogens, or other stimulants, and have various functions such as innate immunity and adaptive immunity, hematopoiesis, cell growth, APSC multifunctional cell and damage tissue repair, etc. Cytokines may be classified into interleukins, interferons, tumor necrosis factor superfamilies, colony stimulating factors, chemotactic factors (chemokines), growth factors, etc. A protein expression tag means an amino acid sequence added at the N-terminus or C-terminus of a target protein, and may be small peptides or long amino acids. Addition of the tag may be advantageous for correct folding of proteins, protein isolation and purification, and intracellular protein degradation. Tags frequently used may include HA, SUMO, His, GST, GFP, and Flag, but are not limited thereto.

There is no limitation in the antibodies applicable to the heterodimeric bispecific antibody of the present disclosure. The antibodies already used in the art for the treatment and/or prevention of diseases may be applied to the present disclosure.

The heterodimeric bispecific antibody of the present disclosure may have one or more substitutions, deletions, additions, and/or insertions. For example, although some amino acids are substituted for the amino acids in the structure of the protein, there is no significant loss of ability to bind to other polypeptides (e.g., antigens) or cells. Since the binding ability and properties of the protein determine the biological functional activity of the protein, substitution of some amino acids on the protein sequence may cause no significant loss of its biological usefulness or activity.

In many cases, polypeptide variants may include one or more conservative substitutions. The "conservative substitution" means that amino acids in the polypeptide variants are replaced by other amino acids having similar properties, such that one skilled in the art of peptide chemistry would expect a secondary structure and hydrophilic nature of the polypeptide to be substantially unchanged.

Amino acid substitutions may be generally based on relative similarity of amino acid side-chain substituents such as hydrophobicity, hydrophilicity, charge, size, etc. Exemplary substitutions that take various characteristics described above into consideration are well known to those skilled in the art and include arginine and lysine; glutamic acid and aspartic acid; serine and threonine; glutamine and asparagine; and valine, leucine, and isoleucine.

As used herein, the term "identity" has the meaning commonly known in the art, and those skilled in the art also are familiar with the rules and criteria for determining identity between different sequences, and the identity refers to the percentage of homology between residues of a polynucleotide or polypeptide sequence variant and residues of a non-variant sequence after aligning the sequences and introducing gaps (if necessary, to achieve the maximum % homology). In the present disclosure, when the definition of identity is satisfied, it is also required that the obtained variant sequence has the biological activity possessed by the parent sequence. Methods and means for screening variant sequences using the above activities are well known to those skilled in the art. Such variant sequences may be readily obtained by those skilled in the art from the teachings herein. In a specific embodiment, the polynucleotide and polypeptide variants have at least about 70%, at least about 75%, at least about 80%, at least about 90%, at least about 95%, at least about 98%, or at least about 99%, or at least about 99.1%, 99.2%, 99.3%, 99.4%, 99.5%, 99.6%, 99.7%, 99.8% or 99.9% polynucleotide or polypeptide identity with the polynucleotide or polypeptide described herein. Due to redundancy of the genetic code, variants of these sequences encoding the same amino acid sequence will exist.

Another aspect provides a polynucleotide composition capable of hybridizing to the polynucleotide sequence provided by the present disclosure or a fragment thereof or a complementary sequence thereof under moderately to highly stringent conditions. Hybridization techniques are well known in the art of molecular biology. For the purposes of explanation, suitable moderately stringent conditions for testing hybridization of the polynucleotide of the present disclosure to another polynucleotide may include pre-washing with a solution of 5×SSC, 0.5% SDS, 1.0 mM EDTA (pH 8.0); performing hybridization in 5×SSC at 50° C. to 60° C. overnight; and washing twice with 2×, 0.5× and 0.2×SSC containing 0.1% SDS for 20 minutes at 65° C., respectively. Those skilled in the art understand that the stringency of hybridization may be readily manipulated, for example, by varying the salt content of the hybridization solution and/or the hybridization temperature. For example, in another embodiment, suitable highly stringent hybridization conditions may include the conditions described above, except for increasing the hybridization temperature, for example, to 60° C. to 65° C. or 65° C. to 70° C.

The host cell of the present disclosure may be any cell which may be used in foreign gene expression, and may include *E. coli*, yeast cells, insect cells, plant cells, and mammalian cells, but is not limited thereto.

The vector of the present disclosure may be a vector which may replicate in any type of cells or organisms, and may include, for example, plasmids, bacteriophages, cosmids, and minichromosomes. In an embodiment, the vector including the polynucleotide of the present disclosure is a vector suitable for propagation or replication of a polynucleotide, or a vector suitable for expression of the polypeptide of the present disclosure. Such vectors are known in the art and are commercially available.

The "vector" may include a shuttle vector and an expression vector. Generally, a plasmid construct may also include an origin of replication (e.g., ColE1 origin of replication) and a selectable marker (e.g., ampicillin or tetracycline resistance) which are for plasmid replication and selection in bacteria, respectively. The "expression vector" refers to a vector including a control sequence or a regulatory element which is required for expression of the antibody of the present disclosure, including antibody fragments, in bacterial or eukaryotic cells.

The vector of the present disclosure may be any vector used for foreign gene expression, and may include, but is not limited to, a plasmid vector, wherein the plasmid vector includes at least an origin of replication, a promoter, a gene of interest, a multiple cloning site, a selection marker gene, and the vector of the present disclosure may include, but is not limited to, a plasmid vector obtained based on pcDNA, such as X0GC vector.

The subject of the present disclosure may include birds, reptiles, mammals, etc. The mammal may include a rodent, a primate. The primate may include a human.

The scope of the diseases involved in the present disclosure may include, but is not limited to, tumors. The tumors may include leukemia, lymphoma, myeloma, brain tumor, head and neck squamous cell carcinoma, non-small cell lung cancer, nasopharyngeal carcinoma, esophageal cancer, stomach cancer, pancreatic cancer, gallbladder cancer, liver cancer, colon cancer, breast cancer, ovarian cancer, cervical cancer, endometrial cancer, uterine sarcoma, prostate cancer, renal cell carcinoma, melanoma.

The pharmaceutically acceptable carrier means a pharmaceutical carrier which is commonly used in the pharmaceutical art, for example, diluents, excipients, water, etc., fillers such as starch, sucrose, lactose, microcrystalline cellulose, etc.; binders such as cellulose derivatives, alginates, gelatin and polyvinylpyrrolidone; wetting agents such as glycerin; disintegrating agents such as sodium carboxymethyl starch, hydroxypropyl cellulose, croscarmellose, agar, calcium carbonate, sodium hydrogencarbonate, etc.; absorption enhancers such as quaternary ammonium compounds; surfactants such as cetanol, sodium lauryl sulfate, etc.; adsorption carriers such as kaolinite, bentonite, etc.; lubricants such as talc, calcium and magnesium stearate, micronized silica gel, polyethylene glycol, etc. In addition, other additives such as flavoring agents, sweeteners, etc. may be added to the composition.

MODE OF DISCLOSURE

Hereinafter, the present disclosure will be described in more detail with reference to the following non-limiting examples. It will be understood by those skilled in the art that various modifications and changes may be made therein without departing from the spirit and scope of the present disclosure, and the modifications and changes are also included in the scope of the present disclosure.

The following experimental methods are all common methods unless otherwise specified, and the experimental materials used may be also easily obtained from commercial companies unless otherwise specified. The various antibodies used in the following Examples of the present disclosure are all standard antibodies obtained from the commercial route.

Example 1: Construction of Vector Structure of Anti-PD-1/Anti-HER2 Heterodimeric Antibody Molecule X0GC expression vectors including heavy chain and light chain of human anti-PD-1(Pem) antibody were constructed, respectively. A sequence of the variable region of the antibody is derived from www.imgt.org/3Dstructure-DB/cgi/details.cgi?pdbcode=9798. A nucleotide sequence of the light chain variable region is the same as in SEQ ID NO: 9 and an amino acid sequence thereof is the same as in SEQ ID NO: 10; a nucleotide sequence of the light chain constant region is the same as in SEQ ID NO: 3 and an amino acid sequence thereof is the same as in SEQ ID NO: 4; a nucleotide sequence of the heavy chain variable region is the same as in SEQ ID NO: 11 and an amino acid sequence thereof is the same as in SEQ ID NO: 12; a nucleotide sequence of the heavy chain constant region is the same as in SEQ ID NO: 13 and an amino acid sequence thereof is the same as in SEQ ID NO: 14. The light chain variable region and the light chain constant region, and the heavy chain variable region and the heavy chain constant region were amplified by PCR, respectively. In all PCR reactions of the present disclosure, Phusion high-fidelity DNA polymerase (F-530L) of NEB, Inc. was used. PCR primers were designed commonly according to the principle of base complementation and the need for restriction enzyme sites. The reaction conditions consisted of 8.9 μl of H$_2$O, 4 μl of 5×Phusion high-fidelity DNA polymerase buffer, 4 μl of 1 mM dNTP, 1 μl of forward primer, 1 μl of reverse primer, 0.1 μl of Phusion high-fidelity DNA polymerase, and 1 μl of the template. PCR products of the variable region and the constant region were electrophoresed on 1.5% agarose gel, and fragments corresponding thereto were recovered using a DNA recovery kit (Promega, A9282, the same applies hereinafter). The recovered variable region fragment and constant region fragment were used as templates and a forward primer of the variable region and a reverse primer of the constant region were used to perform PCR. Fragments corresponding thereto were recovered to obtain a full length fragment of the heavy chain and the light chain. X0GC vector and the full length fragment were digested with EcoRI (NEB, Cat. No. R3101L) and HindIII (NEB, Cat. No. R3104L). The enzyme restriction conditions consisted of 2 μl of 10×buffer 3, each 0.5 μl of EcoRI and HindIII, 3 μl of full length fragment recovered from the gel, and 14.5 μl of H$_2$O. The restriction enzymes were allowed to react at 37° C. for three hours. The restriction products were ligated using T4DNA ligase (NEB, Cat. No. M0202V) (the same applies hereinafter), and the reaction conditions consisted of 2 μl of 10× ligase buffer, 0.5 μl of ligase, 3 μl of the full length fragment recovered from the gel, 3 μl of the X0GC vector recovered from the gel, and 11.5 μl of H$_2$O, which were ligated at room temperature for 12 hours. The ligation product was transformed into *E. coli* competent cell DH5a (Tiangen, CB104, the same applies hereinafter). The X0GC expression vectors of antibody heavy chain and light chain were obtained in order to express the antibody heavy chain and light chain in eukaryotic cells, respectively.

In the present disclosure, another X0GC expression vectors including heavy chain and light chain of anti-human PD-1(BJHM) antibody were also constructed, respectively. A nucleotide sequence of the light chain variable region is the same as in SEQ ID NO: 15 and an amino acid sequence thereof is the same as in SEQ ID NO: 16; a nucleotide sequence of the light chain constant region is the same as in SEQ ID NO: 3 and an amino acid sequence thereof is the same as in SEQ ID NO: 4; a nucleotide sequence of the heavy chain variable region is the same as in SEQ ID NO: 17 and an amino acid sequence thereof is the same as in SEQ ID NO: 18; a nucleotide sequence of the heavy chain constant region is the same as in SEQ ID NO: 13 and an amino acid sequence thereof is the same as in SEQ ID NO: 14. The X0GC expression vectors of antibody heavy chain and light chain were obtained in order to express the antibody heavy chain and light chain in eukaryotic cells, respectively.

In the present disclosure, X0GC expression vectors including heavy chain and light chain of anti-human HER2 antibody were also constructed, respectively. A sequence of the antibody variable region is derived from www-.drugbank.ca/drugs/DB00072, and the heavy chain constant region is human IgG1(Fc2). A nucleotide sequence of the light chain variable region is the same as in SEQ ID NO: 1 and an amino acid sequence thereof is the same as in SEQ ID NO: 2; a nucleotide sequence of the light chain constant region is the same as in SEQ ID NO: 3 and an amino acid sequence thereof is the same as in SEQ ID NO: 4; a nucleotide sequence of the heavy chain variable region is the same as in SEQ ID NO: 5 and an amino acid sequence thereof is the same as in SEQ ID NO: 6; a nucleotide sequence of the heavy chain constant region is the same as in SEQ ID NO: 7 and an amino acid sequence thereof is the same as in SEQ ID NO: 8. The X0GC expression vectors of antibody heavy chain and light chain were obtained in order to express the antibody heavy chain and light chain in eukaryotic cells, respectively.

Example 2: Expression of Anti-PD-1/Anti-HER2 Heterodimeric Antibody Molecule

The expression vectors including the heavy chain and the light chain of anti-human PD-1 antibody were transfected into 293F cells (FREESTYLE™ 293-F Cells, Cat. No. R79007, invitrogen), respectively, and the expression vectors including the heavy chain and the light chain of anti-human HER2 antibody were also transfected into 293F cells, respectively. One day before transfection, cells were seeded. On the day of transfection, cells were collected by centrifugation, and resuspended in fresh FREESTYLE™ 293 expression medium (Cat. No. 12338001, Gibco) at a cell density of 200*10$^5$ cells/mL. The plasmid was added according to the transfection volume, and when a final concentration was 36.67 μg/mL, homogeneous mixing was lightly performed. Next, linear polyethylene imine (PEI, linear, M.W. 25000, Cat. No. 43896, Alfa Aesar) was added, and when a final concentration was 55 μg/mL, homogeneous mixing was lightly performed. Next, the mixture was placed in an incubator, and incubated under shaking at a speed of 120 rpm at 37° C. for 1 hour. Next, 19 times transfection volume of fresh medium was added thereto. Incubation was continuously performed under shaking at a speed of 120 rpm at 37° C. Culture supernatants of the transfected cells incubated for 5 to 6 days were collected by centrifugation.

Expression levels were determined by ELISA. Before purification by applying the culture supernatant to a chromatography column, the precipitate was removed by filtering through a 0.2 μm filter. This procedure was performed at 4° C.

Example 3. Purification of Anti-PD-1/Anti-HER2 Heterodimeric Antibody Molecule Expression Product Purification was performed at 4° C. using an AKTA explorer 100 type protein purification system (GE Healthcare) and affinity chromatography rProtein A SEPHAROSE™ Fast Flow(16 mm I.D., 22 ml, GE Healthcare). First, a mobile phase A (20 mM sodium phosphate buffer, 150 mM sodium chloride, pH 7.4) was used to equilibrate the chromatography column. After a baseline was stabilized, the supernatant of the above treated cells was loaded at a flow rate of 5 mL/min. After loading the sample, equilibration was performed using the mobile phase A. The sample was the anti-PD-1 expression product and the anti-HER2 expression product, respectively. Thereafter, a mobile phase B1 (mobile phase A containing 0.5 M arginine) was used to elute 5 column volumes; 5 column volumes were washed with a mobile phase B2 (100 mM citric acid, pH 3.0) to collect an elution peak, i.e., a peak of the protein of interest; a flow rate during the washing was all 5 ml/min. A chromatogram of the elution peak of anti-PD-1-Fc1 is as shown in FIG. 1, and an elution peak of anti-HER2-Fc2 was also similar thereto (result is not shown). The indicated elution peak (grey area shown) was collected and pH was adjusted to 5.0 by dropwise addition of 1 M sodium acetate solution.

Figure 2:
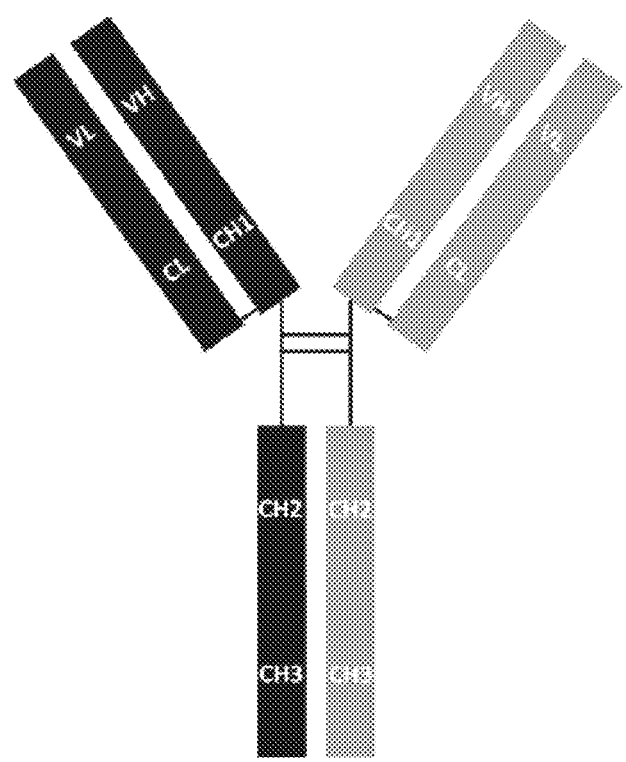
FIG. 2 illustrates a structure of an anti-PD-1/anti-HER2 heterodimeric antibody molecule.

Example 4. Purification of Anti-PD-1/Anti-HER2 Heterodimeric Antibody Molecule The structure of the anti-PD-1/anti-HER2 heterodimeric antibody molecule is as illustrated in FIG. 2.

Figure 3:
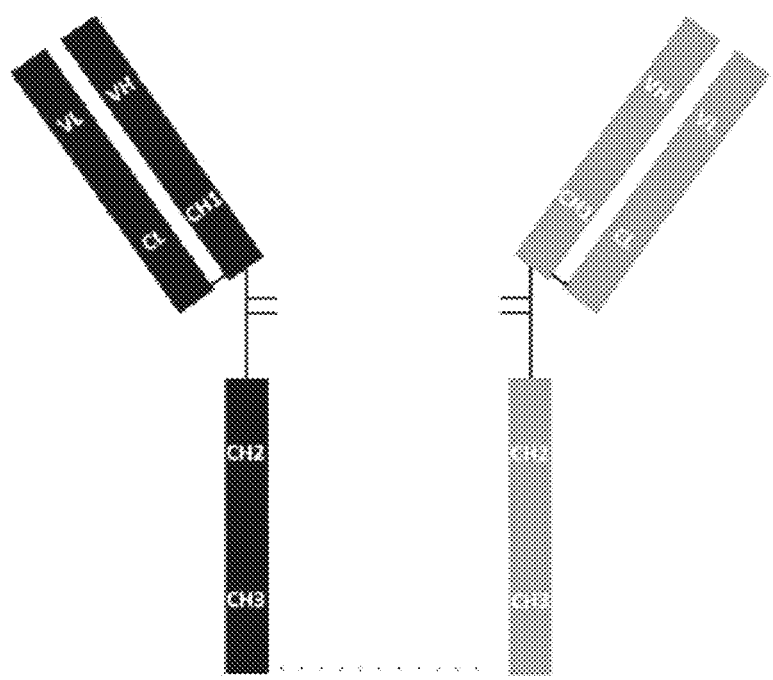
FIG. 3 illustrates a structure of a half-antibody molecule of a heavy chain and a light chain.
Figure 4:
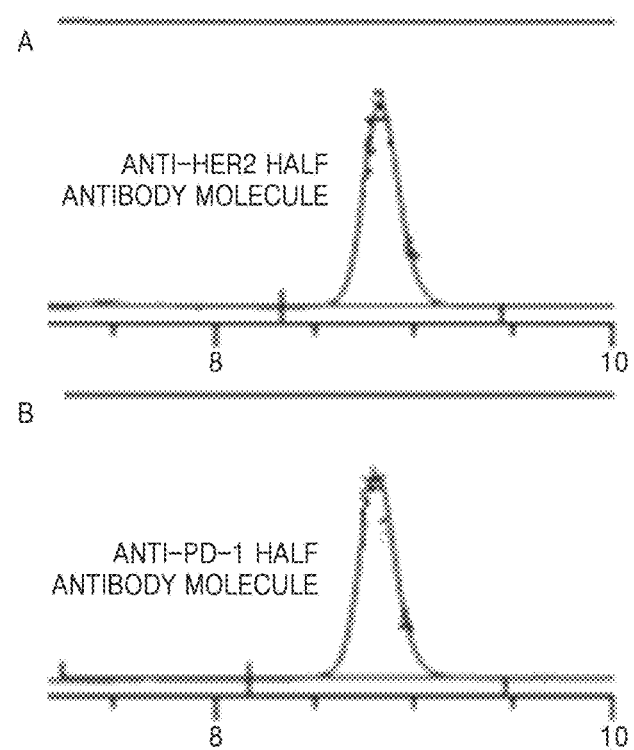
FIG. 4 shows results of size-exclusion chromatography (SEC) analysis of a half-antibody molecule of a heavy chain and a light chain, wherein A and B show analysis results of an anti-HER2 half-antibody molecule and an anti-PD-1 half-antibody molecule, respectively.

The anti-PD-1 and anti-HER2 expression products obtained by the above-described rProtein A SEPHAROSE™ Fast Flow(16 mm I.D., 22 ml, GE Healthcare) method were subjected to in vitro recombination to obtain a heterodimer. First, the protein solutions purified and collected were concentrated by ultrafiltration through an ultrafiltration concentrating tube (nominal molecular weight cut-off of 10 kDa), and the solution was replaced by phosphate buffer saline (PBS) (pH=7.4). The obtained anti-PD-1 and anti-HER2 expression products were adjusted to 1 mg/ml with addition of PBS, and 1/200 times the final volume of 1 M DTT was added such that the final concentration of DTT was 5 mM, respectively. The reduction was carried out at 4° C. (3 hours to 8 hours), and the disulfide bonds were opened through the reduction process, and the disulfide bonds of the hinge region of a small amount of antibody homodimer molecules contained in the anti-PD-1 and anti-HER2 expression products were also opened, thereby forming a half-antibody molecule containing one heavy chain and one light chain, of which structure is as illustrated in FIG. 3. The reduced sample was analyzed by SEC-HPLC containing 1 mM DTT reducing agent in the mobile phase buffer. The results are as shown in FIG. 4. A weight ratio of anti-PD-1 and anti-HER2 homodimers was all less than 10%. Consistent therewith, a weight ratio of the half antibody molecules was all more than 90%.

Figure 5:
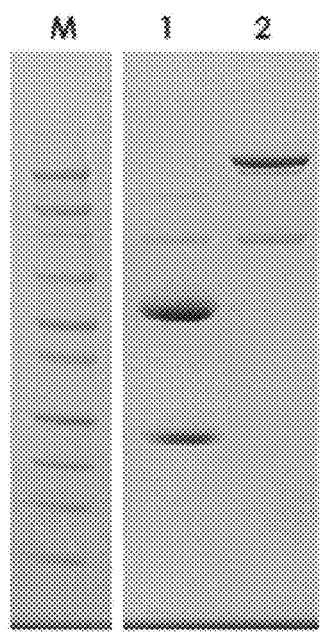
FIG. 5 shows results of SDS-PAGE analysis of oxidized half-antibody molecules of anti-PD-1 and anti-HER2 antibodies.

Thereafter, the reduced anti-PD-1 and anti-HER2 half antibody molecules were mixed according to a molar ratio, and recombination reaction was allowed at 4° C. for 24 hours. During recombination, a heterodimeric bispecific antibody including both the anti-PD-1 and anti-HER2 half antibody molecules was formed via non-covalent interaction between CH2 and CH3 of the anti-PD-1 and anti-HER2 half antibody molecules. Then, the protein solution was concentrated by ultrafiltration through an ultrafiltration concentrating tube (nominal molecular weight cut-off of 10 kDa), and the solution was replaced by PBS (pH=7.4) to terminate the reduction. The solution was subjected to oxidation in the air or with an oxidizing agent to allow formation of disulfide bonds of the heterodimeric bispecific antibody. The oxidation conditions were as follows. 100 mM L-dehydroascorbic acid as the oxidizing agent was added, and when the final concentration of the protein became 1 mg/ml and the final concentration of the oxidizing agent became 1 mM, oxidation was performed at 4° C. for 24 hours. A sample obtained by the above-described oxidation was subjected to SDS-PAGE analysis, and the results are as shown in FIG. 5.

Figure 6:
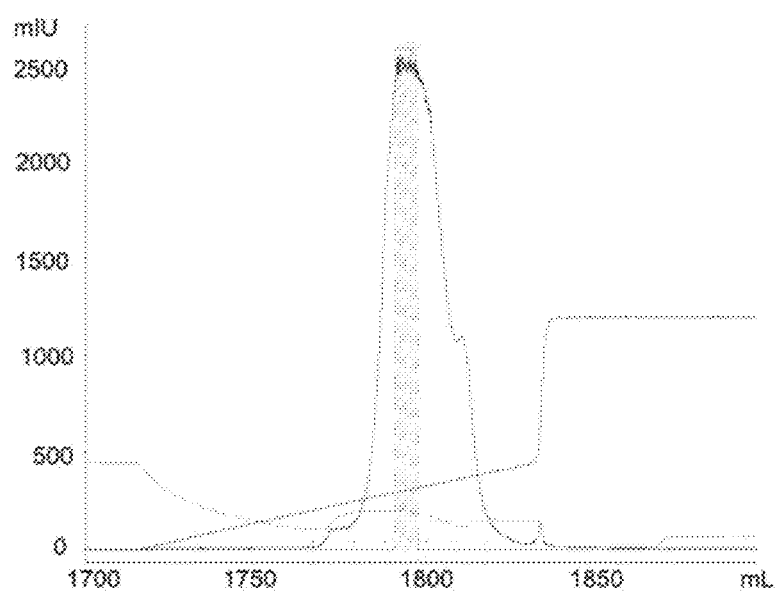
FIG. 6 shows an elution peak of the anti-PD-1/anti-HER2 heterodimeric antibody molecule.
Figure 7:
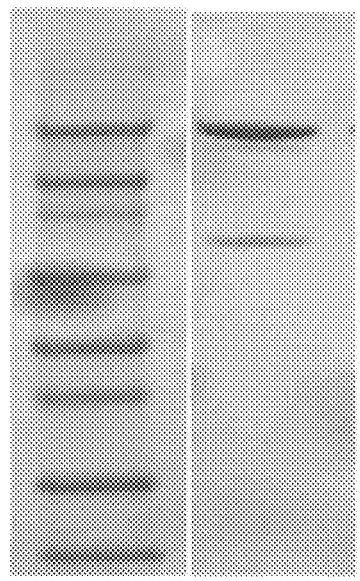
FIG. 7 shows results of SDS-PAGE analysis of the anti-PD-1/anti-HER2 heterodimeric antibody molecule.
Figure 8:
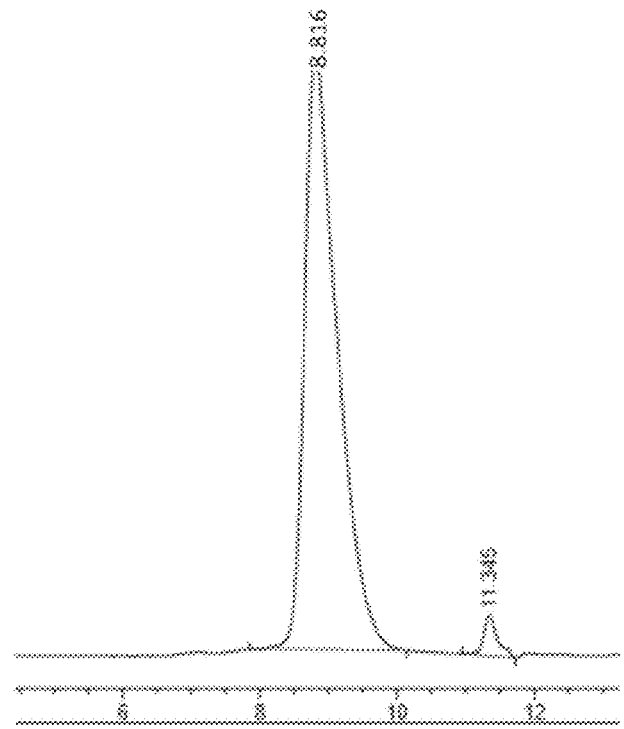
FIG. 8 shows results of SEC analysis of the anti-PD-1/anti-HER2 heterodimeric antibody molecule.

The heterodimer molecules obtained by the above-described reduction/oxidation of the anti-PD-1 and anti-HER2 half antibody molecules were concentrated by ultrafiltration through an ultrafiltration concentrating tube (nominal molecular weight cut-off of 10 kDa), and the solution was replaced by a sodium phosphate buffer solution (pH=5.8). Purification was performed at 4° C. using an AKTA™ explorer 100 type protein purification system (GE Healthcare) and ion chromatography column Source 15S (16 mm I.D., 17 ml, GE Healthcare). First, a mobile phase A (10 mM sodium phosphate, pH 7.0) was used to equilibrate the chromatography column. After a baseline was stabilized, the above-treated protein solution was loaded at a flow rate of 3 ml/min. After loading the sample, equilibration was performed using the mobile phase A. Thereafter, 20 column volumes (0% B-100% B, 170 min, flow rate 2 ml/min) were washed with a gradient of A (10 mM sodium phosphate, pH 5.8) to B (10 mM sodium phosphate, pH 5.8). The indicated elution main peak was collected (see FIG. 6), and the collected protein solution was concentrated by ultrafiltration through an ultrafiltration concentrating tube (nominal molecular weight cut-off of 10 KDa). The solution was replaced by a phosphate solution (PBS, pH=7.4), and filtered and sterilized, and then stored at 4° C. The purified product was analyzed by SDS-PAGE method, and the results are as shown in FIG. 7. As a result of purity analysis by SEC-HPLC, the purity was 97.3%, as shown in FIG. 8.

Figure 9:
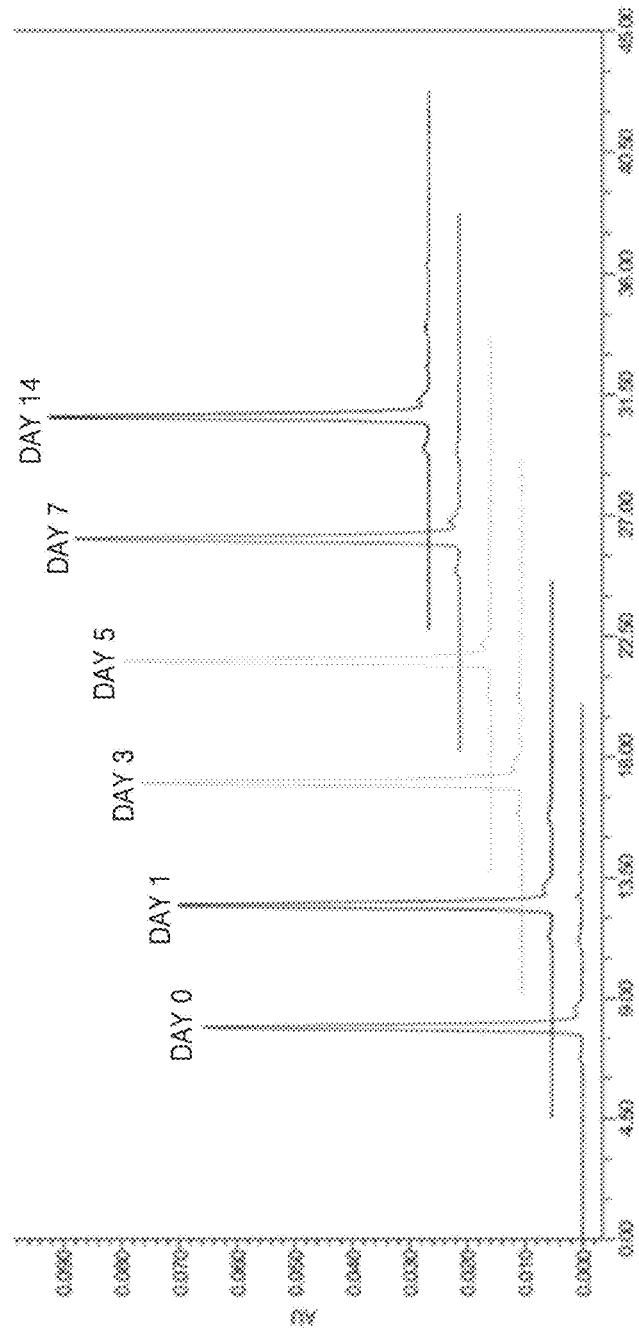
FIG. 9 shows a stability test of the anti-PD-1/anti-HER2 heterodimeric antibody molecule.
Figure 10:
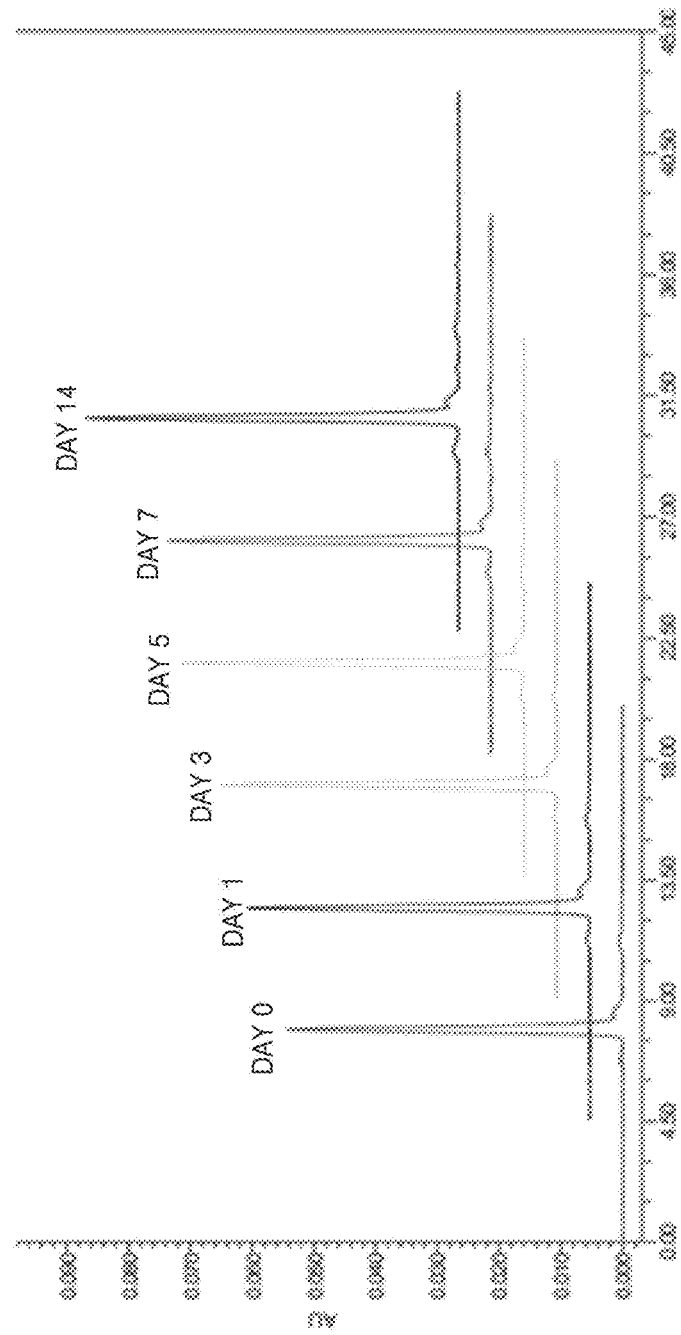
FIG. 10 shows a stability test of the anti-PD-1/anti-HER2 heterodimeric antibody molecule.

Example 5. Stability of Anti-PD-1/Anti-HER2 Heterodimeric Antibody Molecule 10 mg/mL of the PD-1/HER2 heterodimer samples fully sealed was left in a constant climate chamber (BINDER KBF240) at 40° C., and 20 µg of the sample was taken at corresponding time points (baseline (Day 0), after 1 day, 3 days, 5 days, 7 days and 14 days) and separated by size exclusion chromatography (SEC-HPLC). The above SEC-HPLC conditions were as follows: (1) Size exclusion chromatography column: TSKGEL™ G3000SWxl (Tosoh Bioscience), 5 µm, 7.8 mm×30 cm; (2) Mobile phase: 5 mM PBS, 150 mM NaCl, pH 6.7; (3) Flow rate: 0.6 mL/min; (4) UV detection wavelength: 280 nm; (5) Collection time: 30 min. The instrument used was an Agilent 1200 Infinity chromatography, and chromatograph was recorded using an AGILENT CHEMSTATION™ and a ratio of remaining monomers was calculated. As shown in FIGS. 9 (10 mg/mL) and 10 (1 mg/mL), the dimer did not undergo significant aggregation under the experimental conditions of 40° C., and therefore, the PD-1/HER2 heterodimer was considered to have excellent thermal stability.

Example 6. In Vitro Binding Activity of Anti-PD-1/Anti-HER2 Heterodimeric Antibody Molecule The binding ability of the PD-1/HER2 heterodimer antibody to a single antigen was determined by enzyme-linked immunosorbent assay (ELISA).

Detailed procedures are as follows: Recombinant human PD-1 (Beijing Yiqiao Shenzhou, Cat. No. 10377-H08H) or human HER2 (Beijing Yiyi) was coated on a 96-well high adsorption ELISA plate using a carbonate buffer solution of pH 9.6 at a coating concentration of 1 µg/mL and a coating amount of 100 µL per well. The coating was performed at 4° C. overnight. The plate was washed with PBST (phosphate buffered saline with detergent such as TWEEN® 20 or TRITON® X-100) five times. The plate was blocked with 300 µL/well of PBST containing 1% BSA and incubated for 1 hour at 25° C., and washed with PBST five times. A heterodimeric antibody sample and a control each serially diluted with PBST containing 1% BSA were added in an amount of 100 µL per well, and incubated at 25° C. for 1 hour. The plate was washed with PBST five times. Then, horseradish peroxidase-labeled anti-human IgG antibody (Chemicon, Cat. No. AP309P) diluted 1:2000 with PBST containing 1% BSA was added in an amount of 100 µL per well, and incubated at 25° C. for 1 hour. The plate was washed with PBST five times. A colorimetric substrate TMB was added in an amount of 100 µL/well and developed for 10 minutes at room temperature. Color development was terminated by adding 100 µL/well of 1 M $H_2SO_4$. The absorbance at 450 nm was read on a microplate reader.

Figure 11A:
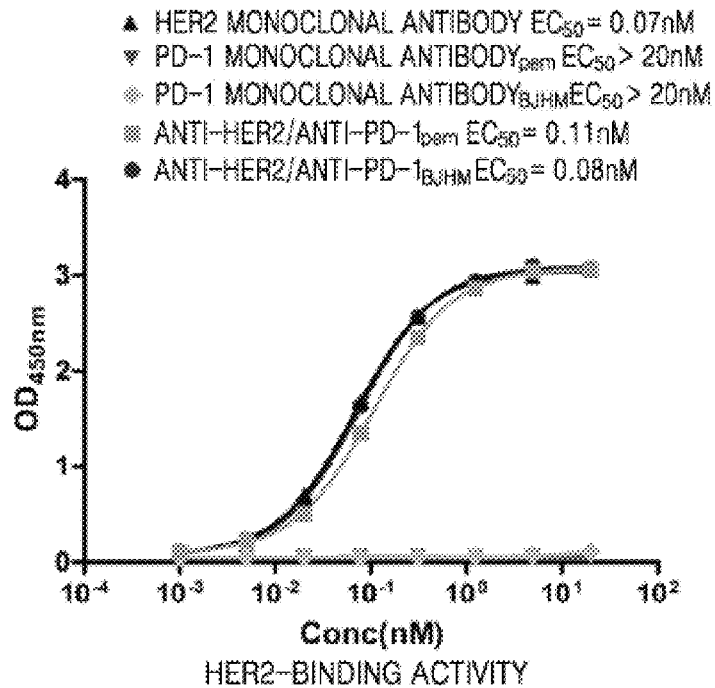
Figure 11B:
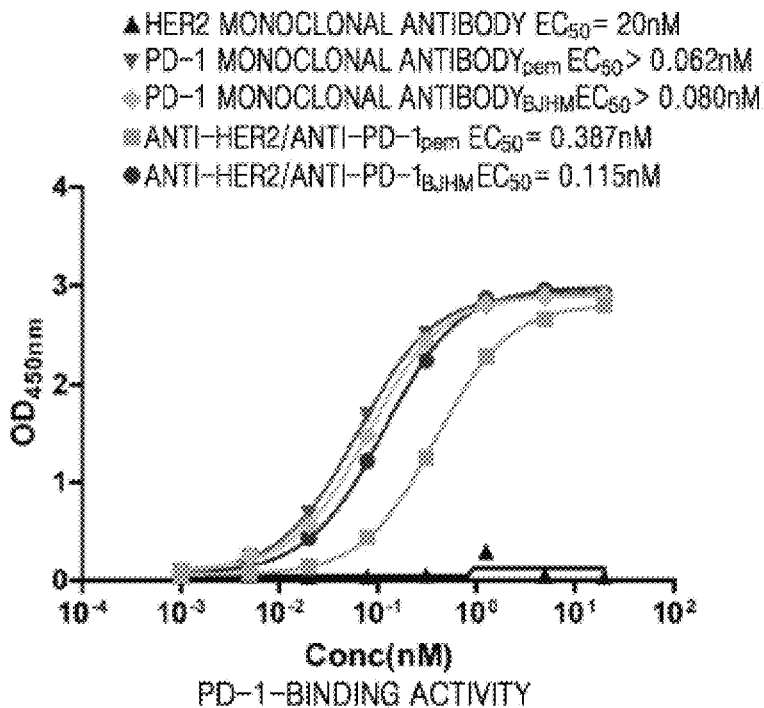

As a result, as shown in FIG. 11, anti-PD-$1_{pem}$/anti-HER2 and anti-PD-$1_{BJHM}$/anti-HER2 all have high affinity for PD-1 and HER2, and the antigen affinity activity of bivalent monoclonal antibody was relatively well maintained. Among them, anti-PD-$1_{BJHM}$/anti-HER2 has stronger PD-1 affinity than anti-PD-$1_{pem}$/anti-HER2.

Example 7. Simultaneous Binding Activity of Anti-PD-1/Anti-HER2 Heterodimeric Antibody Molecule to Dual Target Antigens Simultaneous binding ability of the PD-1/HER2 heterodimeric antibody to dual target antigens was determined on PD-1-overexpressing CHO/PD-1 cells (GenScript, Cat. No. M00529) and HER2-overexpressing SK-BR-3 cells by flow cytometry (FACS).

CHO/PD-1 cells were stained according to a PKH26 kit (Sigma, Cat. No. SLBH4568V) instructions. Briefly, CHO/PD-1 cells were collected, and washed once with serum-free medium. CHO/PD-1 was prepared as a cell suspension of $2×10^7$/mL using Diluent C in the PKH26 kit. PKH26 dye was diluted to 4 µM. Then, they were mixed at 1:1. The mixed suspension had a cell density of $1×10^7$/mL and PKH26 concentration of 2 µM, and incubated for 1 hour at room temperature, and then incubated with an equal volume of FBS for 1 minute, followed by terminating the staining. The suspension was centrifuged at 400 g for 10 minutes, and washed twice with a complete medium, and resuspended in the complete medium for later use. SK-BR-3 cells were stained according to a CFSE (carboxyfluorescein succinimidyl ester) kit (Life technology, Cat. No. C34554) instructions. Briefly, CFSE was diluted with PBS to a working concentration of 0.5 µM and pre-warmed at 37° C. SK-BR-3 cells were collected by centrifugation at 1000 rpm for 5 minutes, and resuspended in the pre-warmed CFSE working solution, followed by incubation at 37° C. for 15 minutes. SK-BR-3 cells were collected by centrifugation at 1000 rpm for 5 minutes, and resuspended in the complete medium, followed by incubation for 30 minutes. The cells were washed once with the complete medium, and resuspended in the complete medium for later use.

The above stained cells were collected by centrifugation and washed once with cold PBS containing 2% FBS. The cells were resuspended in cold PBS containing 2% FBS at a cell density of $5×10^6$/mL. SK-BR-3 and CHO/PD-1 were mixed at 1:1, and then 100 µL thereof was taken from each flow tube (i.e., $2.5×10^5$ of SK-BR-3 and $2.5×10^5$ of CHO/PD-1). Then, 100 µL of the heterodimeric antibody samples diluted with cold PBS containing 2% FBS, a control group, and an isotype control (human immunoglobulin, Jiangxi Boya Biopharmaceutical Co., Ltd., national drug approval No. S19993012) were added at a final concentration of 5 nM, respectively. The flow tube was incubated on ice for 30 minutes, and washed twice with PBS containing 2% FBS.

Figure 12:
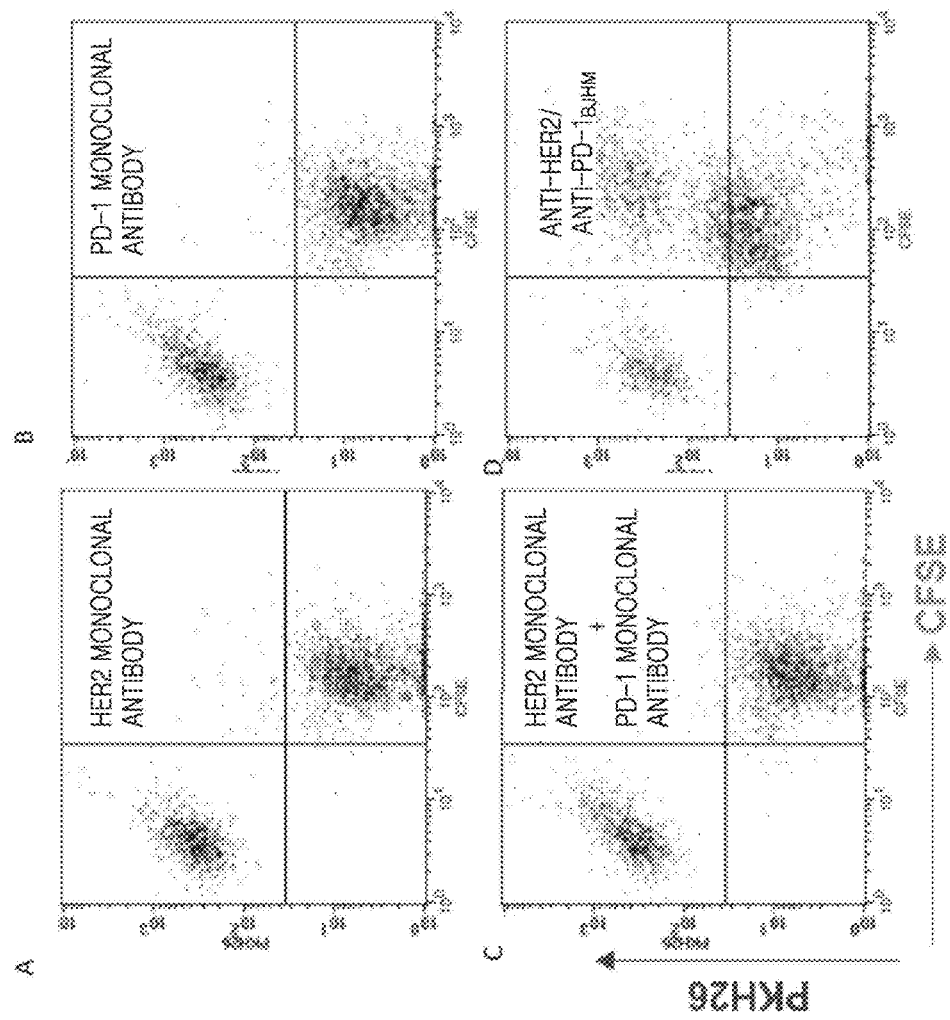
FIG. 12 shows simultaneous binding of the anti-PD-1/anti-HER2 heterodimeric antibody molecule to PD-1-overexpressing CHO/PD-1 cells and HER2-overexpressing SK-BR-3 cells, wherein A to D show simultaneous binding of a HER2 monoclonal antibody, a PD-1 monoclonal antibody, a HER2 monoclonal antibody+PD-1 monoclonal antibody, and anti-PD-1BJHM/anti-HER2, respectively.

As a result, as shown in Table 1 and FIG. 12, simultaneous binding of the heterodimeric antibody to both the PD-1-overexpressing CHO/PD-1 cells and HER2-overexpressing SK-BR-3 cells was observed, suggesting that the PD-1/HER2 heterodimeric antibody is able to trigger a close association between SK-BR-3 and CHO/PD-1 cells, which is the basis for T cell-mediated tumor cell killing.

TABLE 1

Percentage of cells triggering close association

| Name of sample | % associated cells |
|---|---|
| Isotype control | 1.89 |
| HER2 monoclonal antibody(100 nM) | 1.39 |
| PD-1 monoclonal antibody$_{pem}$ (100 nM) | 1.26 |
| PD-1 monoclonal antibody$_{BJHM}$ (100 nM) | 1.43 |
| PD-1 monoclonal antibody + HER2 monoclonal antibody(100 nM) | 1.45 |
| anti-PD-$1_{pem}$/anti-HER2 (100 nM) | 39.71 |
| anti-PD-$1_{BJHM}$/anti-HER2 (0.1 nM) | 8.15 |
| anti-PD-$1_{BJHM}$/anti-HER2 (1 nM) | 32.79 |
| anti-PD-$1_{BJHM}$/anti-HER2 (10 nM) | 36.00 |
| anti-PD-$1_{BJHM}$/anti-HER2 (100 nM) | 38.12 |

Example 8. Blocking Activity of Anti-PD-1/Anti-HER2 Heterodimeric Antibody Molecule Against Binding of PD-1 to PD-L1 or PD-L2 Ligand Recombinant human PD-1-Fc was coated on a 96-well high adsorption ELISA plate using a phosphate buffer solution of pH 9.6 at a coating concentration of 1 μg/mL and a coating amount of 100 μL per well, and the coating was performed at 4° C. overnight. The plate was washed with PBST five times. The plate was blocked with 300 μL/well of PBST containing 1% BSA and incubated for 1 hour at 25° C., and washed with PBST five times. A heterodimeric antibody sample and a control each serially diluted with PBST containing 1% BSA were added, and simultaneously, biotin-labeled PD-L1-Fc at a final concentration of 1 μg/mL or biotin-labeled PD-L2 at a final concentration of 4 μg/mL was added in an amount of 100 μL per well, and incubated at 25 t for 1 hour. The plate was washed with PBST five times. Then, horseradish peroxidase-labeled streptavidin (BD, Cat. No. 554066) diluted 1:1000 with PBST containing 1% BSA was added in an amount of 100 μL per well, and incubated at 25° C. for 1 hour. The plate was washed with PBST five times. A colorimetric substrate TMB was added in an amount of 100 μL/well and developed for 10 minutes at room temperature. Color development was terminated by adding 100 μL/well of 1 M $H_2SO_4$. The absorbance at 450 nm was read on a microplate reader.

Figure 13A:
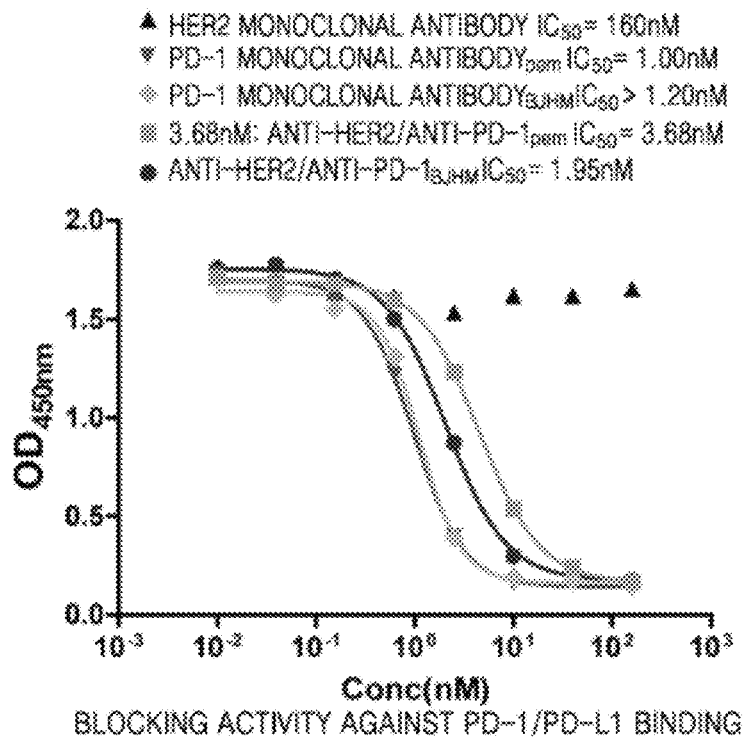
Figure 13B:
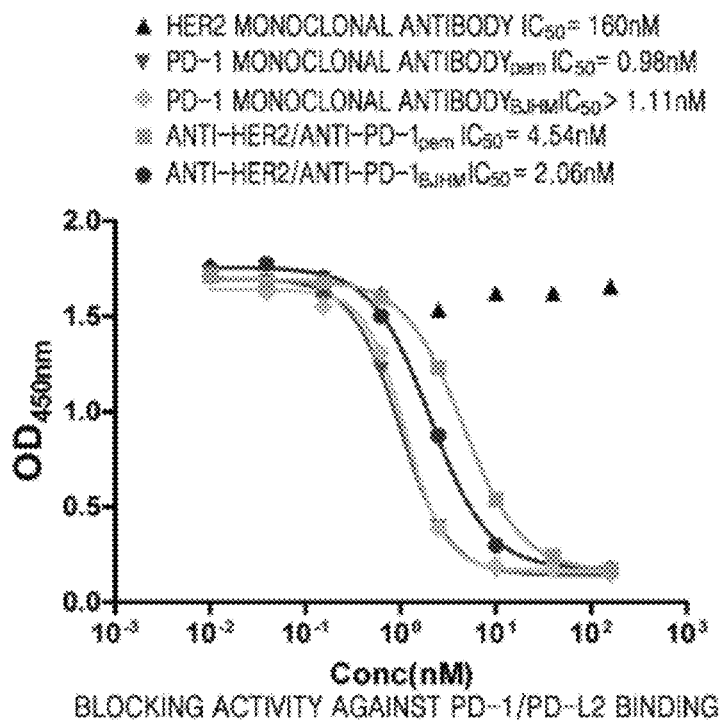

As a result, as shown in FIG. 13, anti-PD-$1_{pem}$/anti-HER2 and anti-PD-$1_{BJHM}$/anti-HER2 all have blocking activity against PD-1/PD-L1 binding and PD-1/PD-L2 binding, and the blocking activity of bivalent monoclonal antibody was relatively well maintained. Among them, anti-PD-$1_{BJHM}$/anti-HER2 has stronger PD-1 blocking activity than PD-$1_{pem}$/anti-HER2.

Example 9. T Cell Cytokine Secretion-Enhancing Activity of Anti-PD-1/Anti-HER2 Heterodimeric Antibody Molecule Human PBMC cells (Lonza, Cat. No. CC-2702) were collected. Human PBMC cells were resuspended in a complete medium (RPMI 1640 containing 10% FBS) at a cell density of $2 \times 10^6$/mL, and 100 μL/well ($2 \times 10^5$ cells per well) of the cells were seeded in a 96-well plates. A PD-1/HER2 heterodimeric antibody sample and a control each diluted with the complete medium were added in an amount of 50 μL per well. PHA (Sigma, Cat. No. L-2769) diluted with the complete medium at a final concentration of 1 μg/mL was added in an amount of 50 μL per well. The plates were incubated in a carbon dioxide incubator at 37° C. After 3 days of incubation, 50 μL of the supernatant was taken and used for detection of cytokine IL-2 (Ray Biotech, Cat. No. ELH-IL2).

Figure 14:
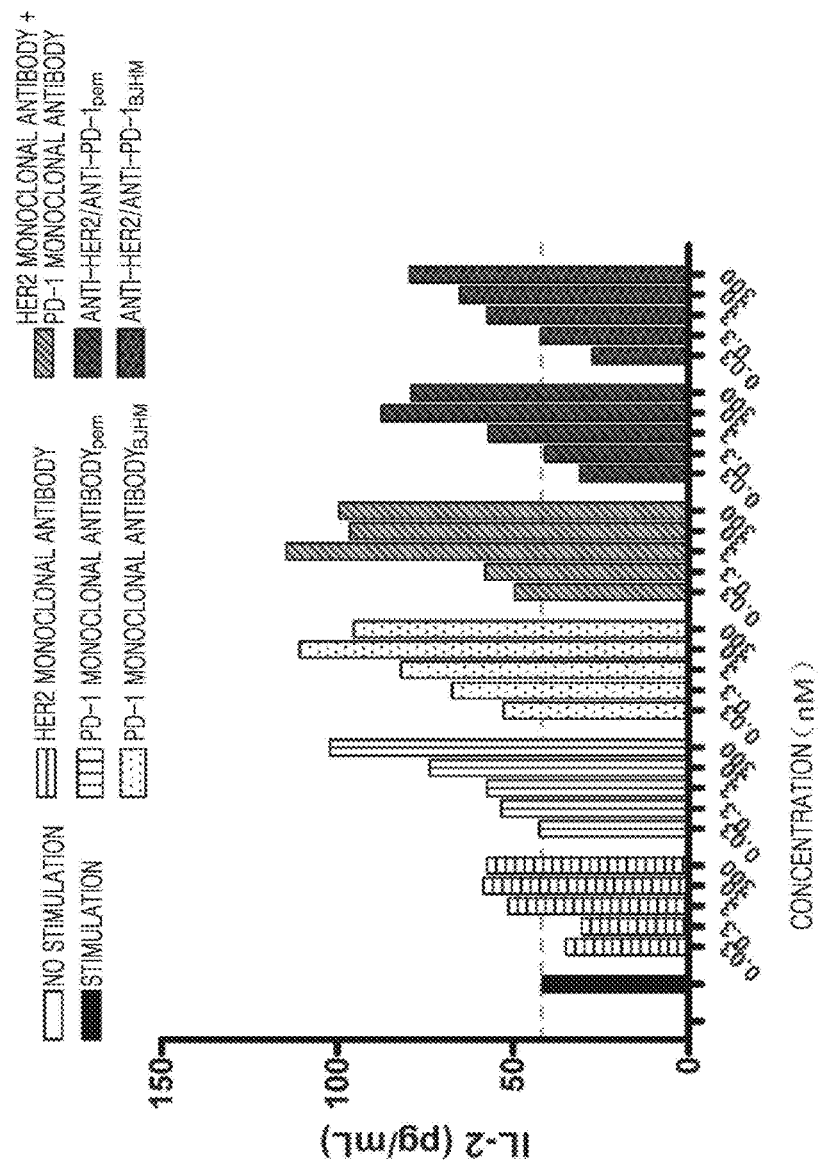
FIG. 14 shows cytokine IL-2 secretion promoted by the anti-PD-1/anti-HER2 heterodimeric antibody molecule.

As shown in FIG. 14, human T cells activate IL-2 secretion under PHA stimulation. Addition of PD-1 antibody enhances T cell activation and promotes cytokine secretion, while the PD-1/HER2 heterodimeric antibody has a similar effect as PD-1 monoclonal antibody, and promotes cytokine IL-2 secretion in a concentration-dependent manner.

Example 10. Pharmacokinetics of Anti-PD-1/Anti-HER2 Heterodimeric Antibody Molecule in Rats 6-8 week-old female SD rats purchased from Beijing Huafukang Biotechnology were used as experimental materials. One week after the rats were acclimated to the environment, they were randomized into groups, each group containing 3 rats. Each group was administered once with PD-1 monoclonal antibody, HER2 monoclonal antibody, PD-1/HER2 heterodimer antibody at a dose of 20 nmol/kg via intravenous route. Immediately after administration, 5 minutes, 30 minutes, 1 hour, 4 hours, 8 hours, 24 hours, 48 hours, 72 hours, 96 hours, 120 hours, 168 hours, 216 hours, 264 hours, 312 hours, 360 hours, 408 hours, and 480 hours after administration, 0.2 mL to 0.3 mL of the blood was collected from the eyelid. The blood samples were left at room temperature for 30 minutes to 1 hour without using an anticoagulant, and after coagulation, the blood samples were centrifuged at 3000 rpm for 10 minutes. The obtained serum samples were frozen and stored at −80° C. until use for a test.

The serum concentrations of PD-1 monoclonal antibody, HER2 monoclonal antibody, and PD-1/HER2 heterodimeric antibody were determined by ELISA. Briefly, human recombinant HER2 protein (Beijing Yiqiao Shenzhou, Cat. No. 10004-H08H) or recombinant PD-1 protein (Beijing Yiqiao Shenzhou, Cat. No. 10377-H08H) was coated on a high adsorption ELISA plate overnight using a carbonate buffer solution of pH 9.6 at 4° C. The plates were washed with PBST. To prevent non-specific binding, the plates were blocked with PBST containing 5% skim milk and washed with PBST. Then, 10% mixed rat serum and the test serum sample diluted with PBST containing 1% BSA were added and incubated at 25° C. for 1 hour, and the plates were washed with PBST. Horseradish peroxidase-labeled anti-human IgG antibody (Chemicon, Cat. No. AP309P) diluted with PBST containing 5% skim milk was added, and incubated at 25° C. for 1 hour. The plates were washed with PBST. Finally, color development was carried out using a colorimetric substrate TMB (3,3',5,5'-tetramethylbenzidine) for 10 minutes at room temperature. Color development was terminated by addition of 1 M $H_2SO_4$. The absorbance at 450 nm was read on a microplate reader.

Figure 15:
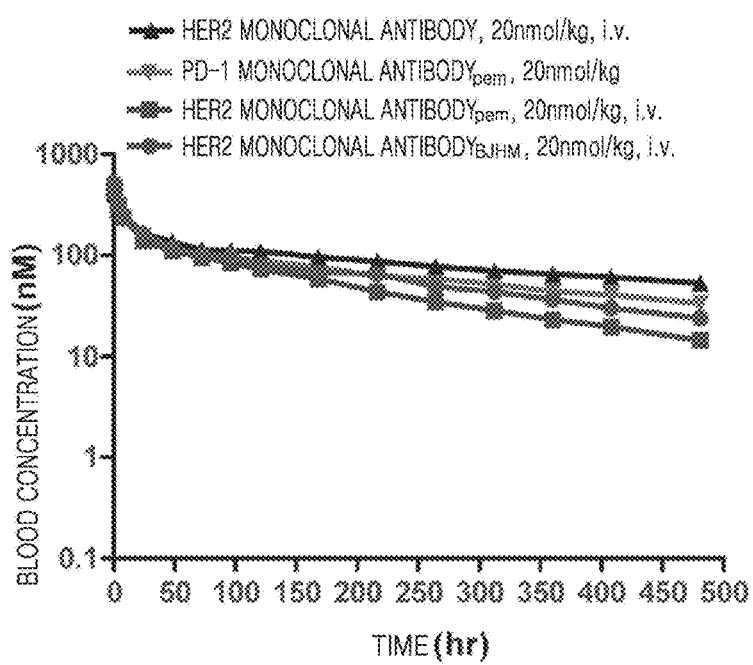
FIG. 15 shows an area under curve (AUC) of the anti-PD-1/anti-HER2 heterodimeric antibody molecule.

As a result, as shown in FIG. 15, 20 nmol/kg of the PD-1/HER2 heterodimeric antibody which was used in the single intravenous injection showed good pharmacokinetic characteristics in rats. The pharmacokinetic parameters of the anti-PD-$1_{BJHM}$/anti-HER2 heterodimeric antibody are as follows: a half-life ($t_{1/2}$) was 207 hours; area under the plasma drug concentration-time curve (AUClast) was 33448 nM·hr; $C_0$ was 534 nM; apparent distribution volume ($V_d$) was 148 mL/Kg; clearance ($C_L$) was 0.50 mL/hr/kg; and a mean residence time ($MRT_{last}$) was 159 hours.

The invention claimed is:

1. A heterodimeric bispecific antibody comprising a first antigen-binding functional domain capable of specifically binding to PD-1 and a second antigen-binding functional domain capable of specifically binding to HER2, wherein the heterodimeric bispecific antibody comprises a first Fc chain and a second Fc chain which are linked to each other via one or more disulfide bonds, the first Fc chain and the second Fc chain being respectively linked to the PD-1 antigen-binding functional domain and the HER2 antigen-binding functional domain via a covalent bond or a linker, or the first Fc chain and the second Fc chain being respectively linked to the HER2 antigen-binding functional domain and the PD-1 antigen-binding functional domain via a covalent bond or a linker, and the first Fc chain and the second Fc chain comprise 5 amino acid substitutions at the following positions:
   amino acid substitutions at positions T366 and D399 of the first Fc chain and amino acid substitutions at positions L351, Y407, and K409 of the second Fc chain,
   wherein the 5 amino acid substitutions comprise
   a) T366L and D399R substitutions in the first Fc chain and L351E, Y407L, and K409V substitutions in the second Fc chain;
   b) T366L and D399C substitutions in the first Fc chain and L351G, Y407L, and K409C substitutions in the second Fc chain;
   c) T366L and D399C substitutions in the first Fc chain and L351Y, Y407A and K409P substitutions in the second Fc chain;
   d) T366P and D399N substitutions in the first Fc chain and L351V, Y407P, and K409S substitutions in the second Fc chain;
   e) T366W and D399G substitutions in the first Fc chain and L351D, Y407P, and K409S substitutions in the second Fc chain;
   f) T366P and D399I substitutions in the first Fc chain and L351P, Y407F, and K409F substitutions in the second Fc chain;
   g) T366V and D399T substitutions in the first Fc chain and L351K, Y407T, and K409Q substitutions in the second Fc chain; or
   h) T366L and D399A substitutions in the first Fc chain and L351W, Y407H, and K409R substitutions in the second Fc chain;
   wherein the amino acid positions are numbered according to the Kabat EU numbering system,
   wherein the PD-1 antigen-binding functional domain comprises
   (i) a heavy chain variable region comprising the sequence of SEQ ID NO: 12 and a light chain variable region comprising the sequence of SEQ ID NO: 10, or
   (ii) a heavy chain variable region comprising the sequence of SEQ ID NO: 18 and a light chain variable region comprising the sequence of SEQ ID NO: 16; and
   wherein the HER2 antigen-binding functional domain comprises
   (i) a heavy chain variable region comprising the sequence of SEQ ID NO: 6, and
   (ii) a light chain variable region comprising the sequence of SEQ ID NO: 2.

2. The heterodimeric bispecific antibody of claim 1, wherein the amino acid substitutions of the first Fc chain are T366L and D399R, and the amino acid substitutions of the second Fc chain are L351E, Y407L, and K409V.

3. The heterodimeric bispecific antibody of claim 1, wherein the first Fc chain and/or the second Fc chain is derived from IgG.

4. The heterodimeric bispecific antibody of claim 1, wherein the PD-1 and HER2 antigen-binding functional domains are Fab fragments or scFv fragments.

5. The heterodimeric bispecific antibody of claim 4, wherein the Fab fragment comprises a first heavy chain variable region and a second heavy chain variable region that are different from each other and a first light chain variable region and a second light chain variable region that are different from each other.

6. The heterodimeric bispecific antibody of claim 1, wherein the PD-1 and HER2 antigen-binding functional domains are all Fab fragments.

7. The heterodimeric bispecific antibody of claim 1, wherein one of the PD-1 and HER2 antigen-binding functional domains is a Fab fragment and the other is a scFv fragment.

8. The heterodimeric bispecific antibody of claim 1, wherein when each of the first Fc chain covalently bonded to the PD-1 antigen-binding functional domain and the second Fc chain covalently bonded to the HER2 antigen-binding functional domain, or each of the first Fc chain covalently bonded to the HER2 antigen-binding functional domain and the second Fc chain covalently bonded to the PD-1 antigen-binding functional domain, is present alone in the presence of a reducing agent, a weight ratio of constituent homodimers is less than 50%.

9. A composition comprising
   the heterodimeric bispecific antibody of claim 1 and a pharmaceutically acceptable carrier.

* * * * *